(12) United States Patent
Chen et al.

(10) Patent No.: US 11,518,993 B2
(45) Date of Patent: Dec. 6, 2022

(54) METHODS AND COMPOSITIONS FOR PREPARING NUCLEIC ACID LIBRARIES

(71) Applicant: Illumina, Inc., San Diego, CA (US)

(72) Inventors: Xi-Jun Chen, San Diego, CA (US); Tarun Khurana, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 102 days.

(21) Appl. No.: 16/494,902

(22) PCT Filed: Mar. 16, 2018

(86) PCT No.: PCT/US2018/022978
§ 371 (c)(1),
(2) Date: Sep. 17, 2019

(87) PCT Pub. No.: WO2018/175258
PCT Pub. Date: Sep. 27, 2018

(65) Prior Publication Data
US 2020/0115707 A1    Apr. 16, 2020

Related U.S. Application Data

(60) Provisional application No. 62/473,595, filed on Mar. 20, 2017.

(51) Int. Cl.
*C12N 15/10* (2006.01)
(52) U.S. Cl.
CPC .................... *C12N 15/1093* (2013.01)
(58) Field of Classification Search
CPC .................................................. C12N 15/1093
See application file for complete search history.

(56) References Cited

U.S. PATENT DOCUMENTS

| | | | |
|---|---|---|---|
| 7,057,026 B2 | 6/2006 | Barnes | |
| 7,211,414 B2 | 5/2007 | Hardin | |
| 7,315,019 B2 | 1/2008 | Turner | |
| 7,329,492 B2 | 2/2008 | Hardin | |
| 7,405,281 B2 | 7/2008 | Xu | |
| 8,829,171 B2 | 9/2014 | Steemers | |
| 9,074,251 B2 | 7/2015 | Steemers | |
| 9,255,265 B2 * | 2/2016 | Stephens et al. .. | C12N 15/1093 |
| 9,790,540 B2 * | 10/2017 | Vaidyanathan et al. .................... | C12Q 1/6806 |

(Continued)

FOREIGN PATENT DOCUMENTS

| | | |
|---|---|---|
| CN | 106 987 585 | 7/2017 |
| WO | WO 1991/06678 | 5/1991 |

(Continued)

OTHER PUBLICATIONS

Bentley et al., Accurate whole human genome sequencing using reversible terminator chemistry, Nature 456:53-59 (2008).

(Continued)

*Primary Examiner* — Richard A Schnizer
*Assistant Examiner* — K. Lau
(74) *Attorney, Agent, or Firm* — Knobbe, Martens, Olson & Bear LLP

(57) ABSTRACT

Systems, methods and compositions provided herein relate to the preparation of nucleic acid libraries. Some embodiments include the preparation of nucleic acid libraries by ligation of single-stranded nucleic acids.

17 Claims, 27 Drawing Sheets

Specification includes a Sequence Listing.

(56) References Cited

U.S. PATENT DOCUMENTS

2007/0031865 A1* 2/2007 Willoughby .............. 435/6
2008/0108082 A1 5/2008 Rank
2014/0128292 A1* 5/2014 Toloue et al. ...... C12N 15/1096
2016/0362680 A1* 12/2016 Armour et al. .... C12N 15/1072

FOREIGN PATENT DOCUMENTS

| WO | WO 2004/018497 | 3/2004 |
| WO | WO 2007/123744 | 11/2007 |
| WO | WO 2012/061832 | 5/2012 |
| WO | WO 2013/022504 | 2/2013 |
| WO | WO 2014/142850 | 9/2014 |
| WO | WO 2017/112666 | 6/2017 |

OTHER PUBLICATIONS

Neiman, et al., Library preparation and multiplex capture for massive parallel sequencing applications made efficient and easy, PLOS One 7(11):1-6 (2012).

Schwartz, et al., Capturing native long-range contiguity by in situ library construction and optical sequencing, PNAS 109(46):18749-18754 (2012).

Shore, et al., Small RNA library preparation method for next-generation sequencing using chemical modifications to prevent adapter dimer formation, PLOS One 11(11):e0167009 (2016).

Vivancos, et al, Stand-specific deep sequencing of the transcriptome, Genome Research 20(7) 989-999 (2010).

* cited by examiner

METHODS AND COMPOSITIONS FOR PREPARING NUCLEIC ACID LIBRARIES

RELATED APPLICATIONS

This application is the U.S. National Phase of PCT Application No. PCT/US2018/022978 filed Mar. 16, 2018 which published in English as WO 2018/175258 on Sep. 27, 2018 which claims priority to U.S. Prov. App. No. 62/473, 595 filed Mar. 20, 2017 entitled "METHODS AND COMPOSITIONS FOR PREPARING NUCLEIC ACID LIBRARIES", the disclosures of which is incorporated herein by reference in their entireties.

SEQUENCE LISTING

The present application includes a sequence listing in Electronic format. The Sequence Listing is provided as a file entitled ILLINC362WOSEQLIST, created Mar. 15, 2018, which is approximately 4 kb in size. The information in the electronic format of the sequence listing is incorporated herein by reference in its entirety.

FIELD OF THE INVENTION

Systems, methods and compositions provided herein relate to the preparation of nucleic acid libraries. Some embodiments include the preparation of nucleic acid libraries by ligation of single-stranded nucleic acids.

BACKGROUND OF THE INVENTION

Several next generation sequencing technologies are available for fast and economical determination of a genome's entire sequence. Typically, a library of template nucleic acids is prepared from a double-stranded target genomic DNA sample prior to sequencing. The sample preparation usually includes a DNA fragmentation step that breaks the larger DNA strands into smaller DNA fragments that are more amenable to next generation sequencing technologies. Oftentimes adaptors are attached to the ends of the DNA fragments, which can be accomplished by DNA end repair followed by adaptor ligation, or more recently by using a transposome system. The use of transposomes, which is a complex of a transposase and transposon sequences, allows for simultaneous genomic fragmentation and adaptor ligation of fragments thereby simplifying library preparation. Library preparation methods are typically labor intensive and require several hands-on steps at different stages.

SUMMARY OF THE INVENTION

Some embodiments include a method of preparing a nucleic acid library, comprising: (a) obtaining a plurality of nucleic acids, wherein the plurality of nucleic acids is single-stranded nucleic acids; (b) dephosphorylating the 5' ends of the single-stranded nucleic acids; (c) ligating a first adaptor to the 3' ends of the single-stranded nucleic acids in the presence of a ligase, wherein the 3' end of the first adaptor comprises a blocking group; (d) phosphorylating the 5' ends of the ligated single-stranded nucleic acids; and (e) ligating a second adaptor to the 5' ends of the phosphorylated ligated single-stranded nucleic acids in the presence of the ligase, thereby obtaining a library of nucleic acids.

In some embodiments, the 5' end of the second adaptor is non-phosphorylated.

In some embodiments, the second adaptor is attached to a substrate. In some embodiments, the substrate comprises a bead or a flow cell.

Some embodiments also include prior to step (e) removing non-ligated single-stranded first adaptors.

Some embodiments also include hybridizing the non-ligated single-stranded first adaptors with a capture probe. In some embodiments, the capture probe comprises a sequence complementary to at least a portion of the first adaptor. In some embodiments, the 3' end of the capture probe comprises a blocking group. In some embodiments, the 5' end of the capture probe comprises a blocking group.

Some embodiments also include digesting the non-ligated single-stranded first adaptors. In some embodiments, digesting the non-ligated single-stranded first adaptors comprises contacting the non-ligated single-stranded first adaptors with a 5'-phophate-dependent exonuclease. In some embodiments, digesting the non-ligated single-stranded first adaptors comprises contacting the non-ligated single-stranded first adaptors with a 5' phosphate-dependent exonuclease and a 5'-deadenylase.

In some embodiments, phosphorylating the 5' end of the ligated single-stranded nucleic acids comprises contacting the ligated single-stranded nucleic acids with a kinase.

Some embodiments include a method of preparing a nucleic acid library, comprising: (a) obtaining a plurality of nucleic acids, wherein the plurality of nucleic acids is double-stranded nucleic acids; (b) contacting the double-stranded nucleic acids with a 5' exonuclease to obtain a plurality of modified double-stranded nucleic acids with single-stranded 3' overhangs; (c) ligating a first adaptor to the 3' ends of the modified double-stranded nucleic acids in the presence of a ligase, wherein the 3' end of the first adaptor comprises a blocking group; (d) dehybridizing the modified double-stranded nucleic acids ligated to the first adaptors to obtain a plurality of single-stranded nucleic acids; and (e) ligating a second adaptor to the 5' ends of the single-stranded nucleic acids in the presence of the ligase, thereby obtaining a library of nucleic acids.

In some embodiments, the 5' end of the second adaptor is non-phosphorylated.

Some embodiments include a method of preparing a nucleic acid library, comprising: (a) obtaining a plurality of nucleic acids, wherein the plurality of nucleic acids is single-stranded nucleic acids; (b) dephosphorylating the 5' ends of the single-stranded nucleic acids; (c) ligating a first adaptor to the 3' ends of the single-stranded nucleic acids in the presence of a ligase, wherein the 3' end of the first adaptor comprises a blocking group; (d) hybridizing the ligated first adaptor with a capture probe; and (e) extending the capture probe, and ligating a second adaptor to the 3' end of the extended capture probe in the presence of the ligase, wherein the 3' end of the second adaptor comprises a blocking group, thereby obtaining a library of nucleic acids.

Some embodiments also include removing the hybridized ligated first adaptor from the extended capture probe.

In some embodiments, the capture probe is attached to a substrate. In some embodiments, the substrate comprises a bead or a flow cell. In some embodiments, the capture probe comprises a capture probe index. In some embodiments, the capture probe comprises a cleavable linker. Some embodiments also include cleaving the cleavable linker.

Some embodiments include a method of preparing a nucleic acid library, comprising: (a) obtaining a plurality of nucleic acids, wherein the plurality of nucleic acids is single-stranded nucleic acids; (b) dephosphorylating the 5' ends of the single-stranded nucleic acids; (c) ligating a linker to the 3' ends of the single-stranded nucleic acids, wherein the linker comprises a first adaptor and a second adaptor, and the 3' end of the linker comprises a blocking group; (d) phosphorylating the 5' ends of the ligated single-stranded nucleic acids; and (e) deprotecting the 3' ends of the phosphorylated nucleic acids, and circularizing the deprotected nucleic acids by ligation, thereby obtaining a library of circular nucleic acids.

In some embodiments, the linker comprises a cleavable site between the first adaptor and the second adaptor.

Some embodiments also include linearizing the circular nucleic acids by cleavage at the cleavable linker. In some embodiments, the cleavable site comprises an uracil residue. Some embodiments also include contacting the circular nucleic acids with an uracil-specific excision reagent. In some embodiments, the uracil-specific excision reagent comprises an enzyme selected from uracil DNA glycosylase (UDG) and DNA glycosylase-lyase endonuclease VIII.

Some embodiments also include amplifying the circular nucleic acids by a method comprising hybridizing at least a primer to the first adaptor or the second adaptor. In some embodiments, the amplification is selected from PCR and rolling circle amplification (RCA). In some embodiments, the amplification comprises contacting the circular nucleic acids with a polymerase that forms a linear product on contacting an uracil residue in a template.

In some embodiments, dephosphorylating the 5' end of the single-stranded nucleic acids comprises contacting the single-stranded nucleic acids with a phosphatase.

In some embodiments, steps (b)-(e) are performed in a single reaction volume.

In some embodiments, steps (b)-(e) are performed in a single reaction vessel.

In some embodiments, the first adaptor and/or second adaptor comprises a sequencing primer binding site.

In some embodiments, the first adaptor comprises a P7 sequence, a P5 sequence, or a complement or reverse complement thereof. In some embodiments, the second adaptor comprises a P7 sequence, a P5 sequence, or a complement or reverse complement thereof.

In some embodiments, the first adaptor and/or second adaptor comprises an adaptor index. In some embodiments, the first adaptor index is different from the second adaptor index. In some embodiments, the adaptor index is indicative of the source of the plurality of nucleic acids.

In some embodiments, the blocking group comprises a 3'-spacer C3 or a dideoxynucleotide.

In some embodiments, the ligase comprises a single-stranded nucleic acid ligase.

In some embodiments, the ligation of the first adaptor and/or the ligating of the second adaptor is performed in the presence of a volume excluding agent. In some embodiments, the volume excluding agent is selected from the group consisting of a polyethylene glycol (PEG), dextran, hetastarch, a neutral, highly branched, high-mass, hydrophilic polysaccharide (FICOLL), and polyvinylpyrrolidone. In some embodiments, the first ligation step and/or second ligation step is performed in a reaction volume comprising at least about 37% (wt/vol) PEG. In some embodiments, the first ligation step and/or second ligation step is performed in a reaction volume comprising at least about 60% (wt/vol) PEG.

In some embodiments, the plurality of nucleic acids comprises RNA. In some embodiments, the plurality of nucleic acids comprises cDNA or genomic DNA.

In some embodiments, the average size of a nucleic acid of the plurality of nucleic acids is less than about 200 nucleotides.

In some embodiments, the plurality of nucleic acids is obtained from a low quality nucleic acid source. In some embodiments, the plurality of nucleic acids is obtained from a fixed sample.

Some embodiments also include amplifying the library of nucleic acids.

Some embodiments also include obtaining sequence data from the library of nucleic acids.

Some embodiments include a nucleic acid library prepared by a method of any one of the foregoing embodiments.

Some embodiments include a kit comprising: a first adaptor wherein the 3' end of the first adaptor comprises a blocking group, wherein the first adaptor comprises a P7 sequence, a P5 sequence, or a complement or reverse complement thereof; a ligase; and a component selected from the group consisting of a volume excluding agent, a kinase, a phosphatase, a 5' phosphate-dependent exonuclease, 5' deadenylase, a polymerase that forms a linear product on contacting an uracil residue in a template, an uracil-specific excision reagent, and a second adaptor, wherein the second adaptor comprises a P7 sequence, a P5 sequence, or a complement or reverse complement thereof. In some embodiments, a linker comprises the first and the second adaptors.

Some embodiments include a reaction vessel comprising a reaction volume comprising: a plurality of nucleic acids; a first adaptor wherein the 3' end of the first adaptor comprises a blocking group; a ligase; and a volume excluding agent.

In some embodiments, the plurality of nucleic acids is single-stranded nucleic acids.

In some embodiments, the first adaptor is ligated to the 3' ends of the plurality of single-stranded nucleic acids, thereby forming a plurality of modified single-stranded nucleic acids.

In some embodiments, a non-ligated first adaptor is hybridized to a capture probe. In some embodiments, the capture probe comprises a sequence complementary to at least a portion of the first adaptor.

In some embodiments, the plurality of nucleic acids is double-stranded nucleic acids having 3' overhangs. In some embodiments, the first adaptor is ligated to the 3' ends of the plurality of double-stranded nucleic acids having 3' overhangs, thereby forming a plurality of modified double-stranded nucleic acids.

Some embodiments also include a second adaptor. In some embodiments, the 5' end of the second adaptor is non-phosphorylated.

Some embodiments also include a dephosphorylating agent. In some embodiments, the dephosphorylating agent comprises a phosphatase. In some embodiments, the phosphatase is inactivated.

In some embodiments, the volume excluding agent is selected from the group consisting of a polyethylene glycol (PEG), dextran, hetastarch, a neutral, highly branched, high-mass, hydrophilic polysaccharide (FICOLL), and polyvinylpyrrolidone. In some embodiments, the reaction volume comprises at least about 37% (wt/vol) PEG. In some embodiments, the reaction volume comprises at least about 60% (wt/vol) PEG.

In some embodiments, the first adaptor and/or second adaptor comprises a sequencing primer binding site.

In some embodiments, the first adaptor and/or second adaptor comprises an adaptor index. In some embodiments, the first adaptor index is different from the second adaptor index. In some embodiments, the adaptor index is indicative of the source of the plurality of single-stranded nucleic acids.

In some embodiments, the blocking group comprises a 3'-spacer C3 or a dideoxynucleotide. In some embodiments, the blocking group comprises a 3'-spacer C3.

In some embodiments, the ligase wherein the ligase comprises a single-stranded nucleic acid ligase.

In some embodiments, the plurality of nucleic acids comprises RNA. In some embodiments, the plurality of nucleic acids comprises cDNA or genomic DNA.

In some embodiments, the plurality of single-stranded nucleic acids is obtained from a low quality nucleic acid source. In some embodiments, the plurality of nucleic acids is obtained from a fixed sample.

Some embodiments include a flow cell comprising the reaction vessel of any one of the foregoing embodiments.

Some embodiments include a system comprising the reaction vessel of any one of the foregoing embodiments, and a detector for obtaining sequencing data.

BRIEF DESCRIPTION OF THE DRAWINGS

In FIG. 5, a capture probe having a P7 sequence hybridizes to the P7' adaptor ligated using TS2126 RNA ligase (CIRCLIGASE™) to the target nucleic acid, and to excess non-ligated P7' adaptors. Hybridization of the capture probe to non-ligated P7' adaptors inhibits ligation of the non-ligated P7' adaptors to other nucleic acids.

DETAILED DESCRIPTION

Embodiments of the systems, methods, and compositions provided herein relate to the preparation of nucleic acid libraries. Some embodiments include the ligation of single-stranded nucleic acids to adaptors to prepare libraries of nucleic acids from small amounts of source nucleic acids. Some embodiments include the ligation of double-stranded nucleic acids having 3' overhangs to adaptors to prepare libraries of nucleic acids from small amounts of source nucleic acids. Some embodiments include the ligation of single-stranded nucleic acids to linkers comprising adaptors to prepare libraries of circular nucleic acids from small amounts of source nucleic acids.

In one embodiment, single-stranded nucleic acids are prepared by reducing the likelihood of self-concatemerization of reaction species. For example, to ligate a 3' adaptor to the 3' end of a single-stranded nucleic acid, the 3' adaptor can have a blocking group that inhibits self-concatemerization. Similarly, the 5' end of the single-stranded nucleic acid can be dephosphorylated to inhibit self-concatemerization. Ligation products from this reaction would include a ligated single-stranded nucleic acid having a 3' blocking group. In some embodiments, ligation of a 3' adaptor to the 3' end of a single-stranded nucleic acid was found to be highly efficient and performed in the presence of a volume excluding agent. The 5' end of the ligated single-stranded nucleic acid having a 3' blocking group can be dephosphorylated so that a 5' adaptor can be ligated to its 5' end. To ligate a 5' adaptor to the 5' end of the re-phosphorylated ligated single-stranded nucleic acid having a 3' blocking group, the 5' adaptor can have a dephosphorylated 5' end to inhibit self-concatemerization. The ligation product from this reaction would include a single-stranded nucleic acid having a 5' adaptor and a 3' adaptor. Adaptors can include sequencing primer sites, amplification primer sites, and indexes. As used herein an "index" can include a sequence of nucleotides that can be used as a molecular identifier and/or barcode to tag a nucleic acid, and/or to identify the source of a nucleic acid. In some embodiments, an index can be used to identify a single nucleic acid, or a subpopulation of nucleic acids. In some embodiments, single-stranded nucleic acid libraries can be prepared in a single reaction vessel, in a single volume. In addition, embodiments provided herein may reduce the likelihood of primer-dimer products forming in subsequent amplification reactions.

Figure 1:
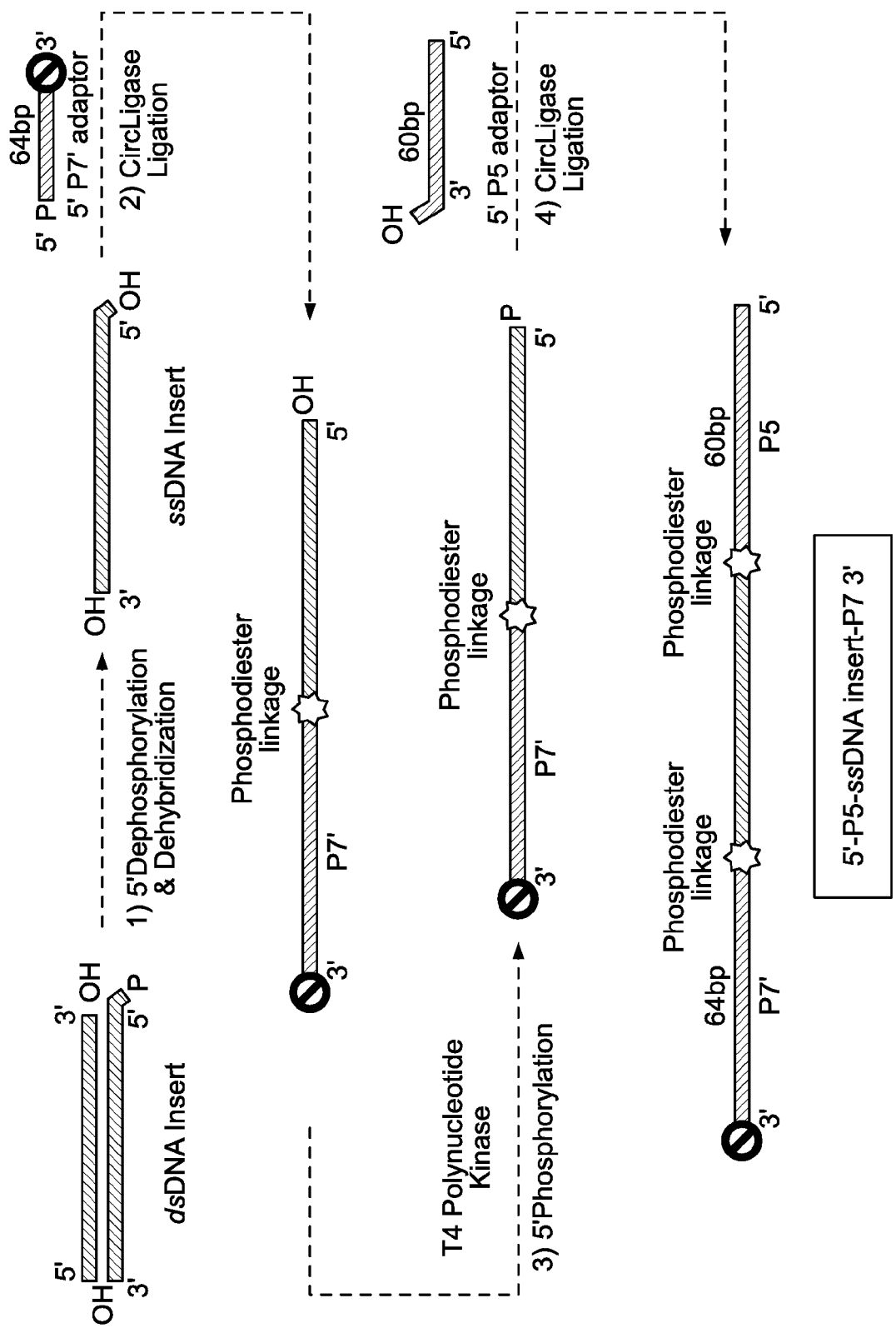
FIG. 1 is a schematic outline for a method to prepare a library of single-stranded nucleic acids according to one embodiment. A double-stranded nucleic acid is dehybridized to form a single-stranded nucleic acid, and a library can be prepared by dephosphorylating the 5' end of the single-stranded nucleic acid, ligating a P7' adaptor containing a 3' blocking group to the 3' end of the single-stranded nucleic acid using TS2126 RNA ligase (CIRCLIGASE™), re-phosphorylating the 5' end of a ligated single-stranded nucleic acid, and ligating a P5 adaptor containing a non-phosphorylated 5' end to the 5' end of a ligated single-stranded nucleic acid.

An example method according to one embodiment is outlined in FIG. 1. As illustrated, the 5' ends of target single-stranded nucleic acids are dephosphorylated to prevent the formation of concatemers in subsequent ligation steps. First adaptors are ligated to the 3' ends of the dephosphorylated targets using a single-stranded ligase. To prevent the first adaptors from forming concatemers, the 3' ends of the first adaptors can be blocked. The 5' ends of ligated targets are re-phosphorylated with a kinase, and a second adaptor is ligated to the 5' ends of the dephosphorylated targets using the single-stranded ligase, thereby forming a library of nucleic acids. To prevent the second adaptors from forming concatemers, the 5' ends of the second adaptors can be non-phosphorylated.

Figure 2:
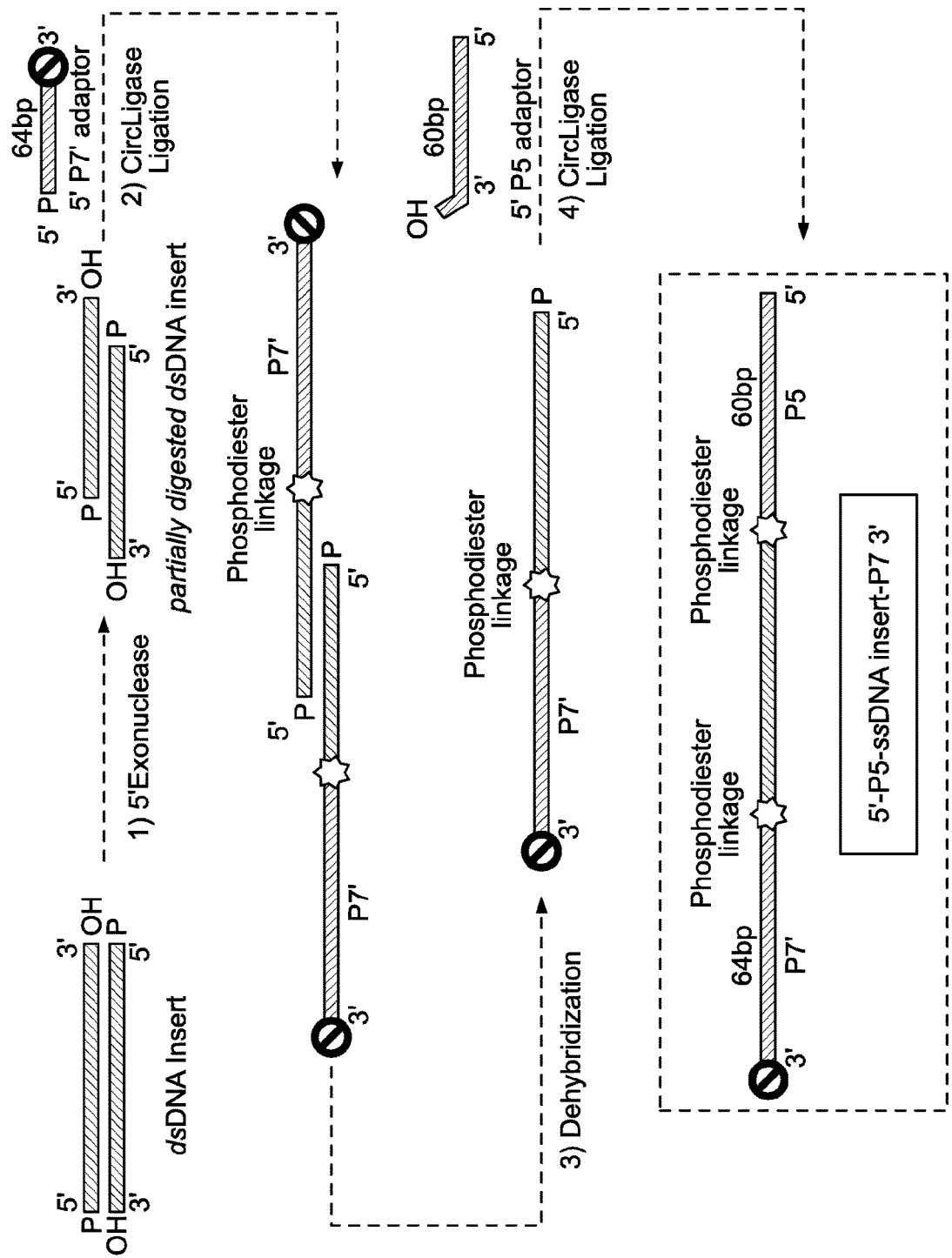
FIG. 2 is a schematic outline for a method to prepare a library of single-stranded nucleic acids according to one embodiment. A double-stranded nucleic acid is partially digested with a 5' exonuclease to form a double-stranded nucleic acid with 3' overhangs. A P7' adaptor containing a 3' blocking group can be ligated using TS2126 RNA ligase (CIRCLIGASE™) to the 3' ends of double-stranded nucleic acid with 3' overhangs, the ligated double-stranded nucleic acid with 3' overhangs can be dehybridized to form single-stranded nucleic acids, and a P5 adaptor containing a non-phosphorylated 5' end can be ligated to the 5' end of a ligated single-stranded nucleic acid.

Another example method according to one embodiment is outlined in FIG. 2 in which adaptors are ligated to double-stranded nucleic acids having 3' overhangs. In some embodiments, a first adaptor can be ligated to the 3' ends of the double-stranded nucleic acids having 3' overhangs. To prevent the first adaptors from forming concatemers, the 3' ends of the first adaptors can be blocked. The double-stranded nucleic acids ligated to the first adaptors can be dehybridized to obtain a plurality of single-stranded nucleic acids. A second adaptor can be ligated to the 5' ends of the single-stranded nucleic acids.

Figure 3:
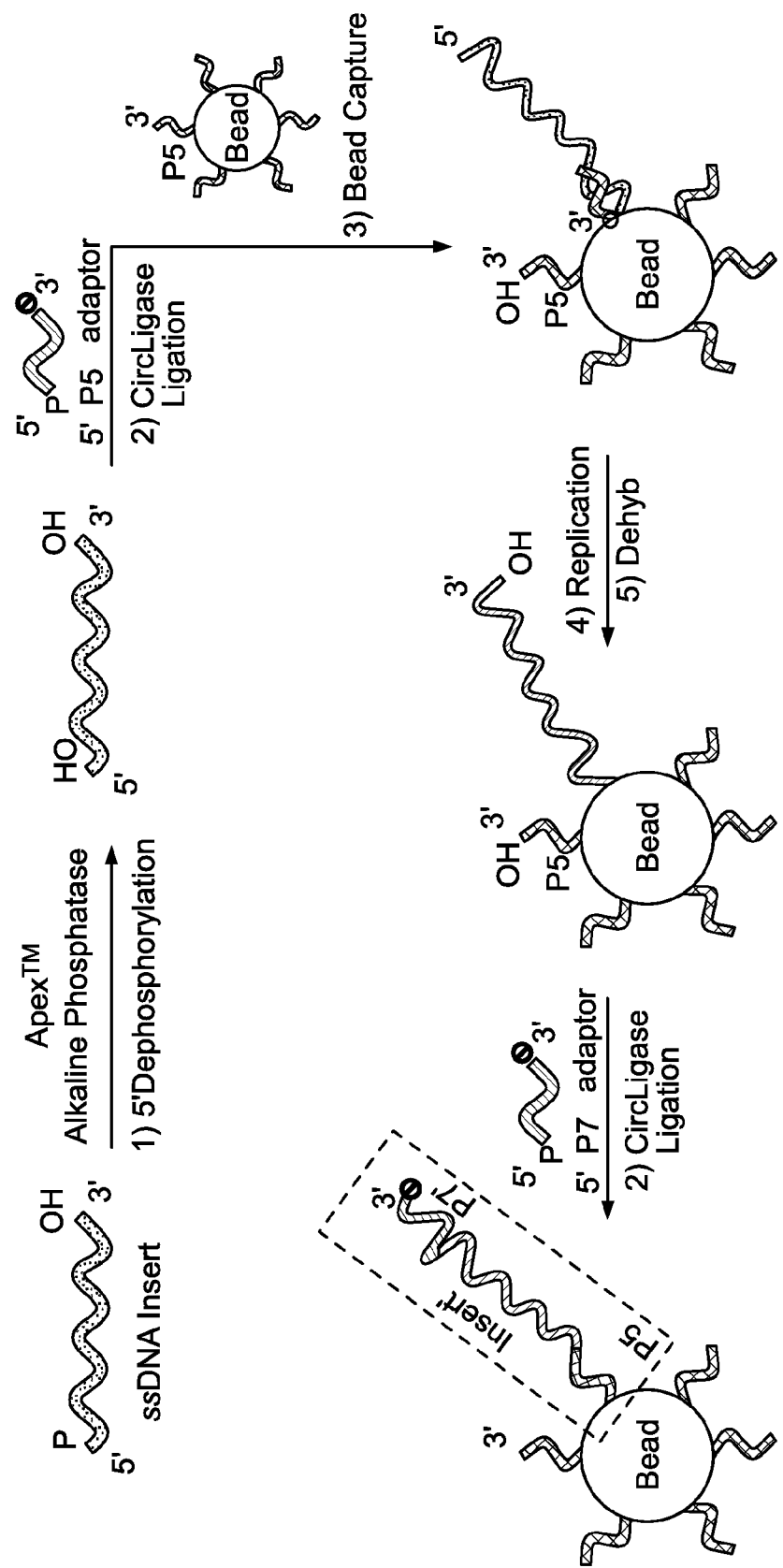
FIG. 3 depicts a schematic outline for a method to prepare a library of single-stranded nucleic using beads according to one embodiment. A library can be prepared by dephosphorylating using a heat-labile alkaline phosphatase (APEX™ phosphatase) the 5' end of a single-stranded nucleic acid, ligating using TS2126 RNA ligase (CIRCLIGASE™) a P5' adaptor containing a 3' blocking group to the 3' end of the single-stranded nucleic acid, hybridizing the first ligation product to a P5 capture probe attached to a bead, extending the capture probe, removing the hybridized first ligation product from the extended capture probe, and ligating a P7' adaptor containing a 3' blocking group to the 3' end of the extended capture probe.

Another example method according to one embodiment is outlined in FIG. 3 in which a library of nucleic acids can be prepared using adaptors attached to beads. In some such embodiments, a first adaptor is ligated to the 3' ends of dephosphorylated targets using a single-stranded ligase. The ligated first adaptors can be hybridized to capture probes attached to beads. The capture probes can be extended, and a second adaptor can be ligated to the extended capture probe. Non-ligated single-stranded adaptors can be removed by washing from the beads. Some embodiments for preparing a library of nucleic acids that include the use of adaptors attached to beads are useful to add indexes to nucleic acid libraries. For example, a first adaptor comprising a first index can be attached to a bead, and a second adaptor comprising a second index and a capture probe can be ligated to the first adaptor. A target nucleic acid hybridized to the capture probe can be extended to incorporate the first and second index.

Figure 4A:
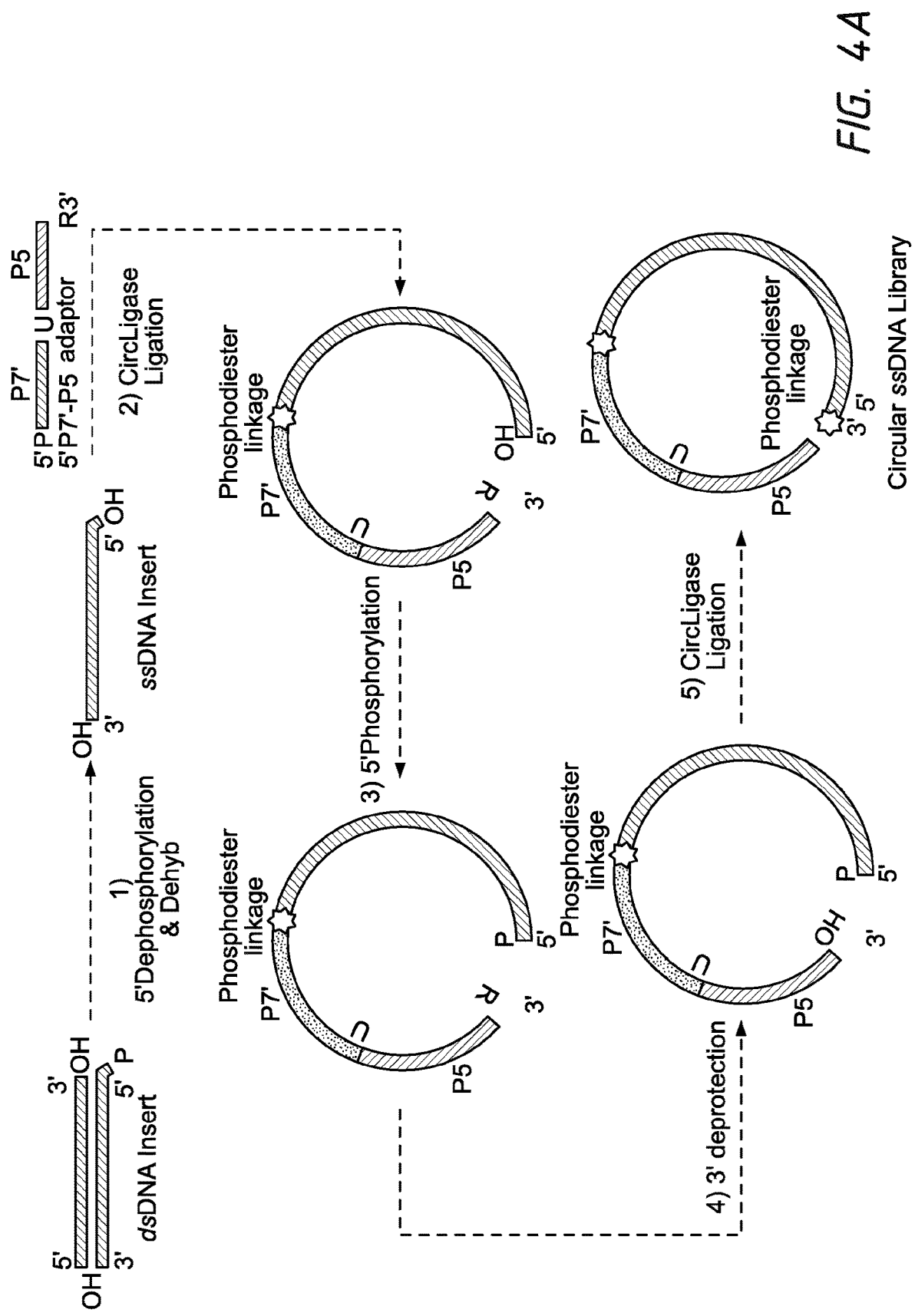
FIG. 4A is a schematic outline for a method to prepare a library of circular single-stranded nucleic acids according to one embodiment. A double-stranded nucleic acid is dehybridized to form a single-stranded nucleic acid, and a library can be prepared by dephosphorylating the 5' end of the single-stranded nucleic acid; ligating using TS2126 RNA ligase (CIRCLIGASE™) a linker comprising a P7' adaptor, a cleavable site ("U"), a P5 adaptor having a 3' blocking group ("R"), to the 3' end of the single-stranded nucleic acid; re-phosphorylating the 5' end of a ligated single-stranded nucleic acid; deprotecting the 3' end of the ligated single-stranded nucleic acid, and circularizing the deprotected nucleic acids to form a member of a library comprising circular single-stranded nucleic acids.

Another example method according to one embodiment is outlined in FIG. 4A in which a library of single-stranded circular nucleic acids can be prepared using a linker comprising first and second adaptors. In some such embodiments, the linker can include a cleavable site between the first adaptor and the second adaptor, such that cleavage of the cleavable site of a circular nucleic acid can result in a linear nucleic acid having the first adaptor at one end, and the second adaptor at the other end of the linear nucleic acid.

In some embodiments, a library of nucleic acids may be amplified using primer sites in the adaptor sequences. In some embodiments, the efficiency of subsequent amplification steps can be reduced by the formation of primer-dimers. To increase the efficiency of subsequent amplification steps, non-ligated single-stranded adaptors can be removed from ligation products. An example outlined in FIG. 5, and described further herein, includes removal of non-ligated single-stranded first adaptors by hybridization with capture probes. Another example outlined in FIG. 6, and described further herein, includes removal of non-ligated single-stranded first adaptors by digestion with the use of a 5' phosphate-dependent exonuclease and 5'-deadenylase.

Preparing Single-Stranded Libraries

Some embodiments of the systems, methods and compositions provided herein include methods in which adaptors are ligated to target nucleic acids. Some embodiments provided herein to prepare nucleic acids libraries provided herein can advantageously be performed in a single reaction volume.

Adaptors include nucleic acids, such as single-stranded nucleic acids. Adaptors can include short nucleic acids having a length less than, greater than, or equal to about 5 nucleotides, 10 nucleotides, 20 nucleotides, 30 nucleotides, 40 nucleotides, 50 nucleotides, 60 nucleotides, 70 nucleotides, 80 nucleotides, 90 nucleotides, 100 nucleotides, or a range between any two of the foregoing sizes. Adaptors can include sequencing primer binding sites, amplification primer binding sites, and/or indexes. For example, an adaptor can include a P5 sequence, a P7 sequence, or a complement thereof. Indexes can be useful to identify the source of a nucleic acid molecule. Examples of the use and preparation of indexes useful with embodiments provided herein can be found in Int. Pub. Nos. WO 2012/061832 and WO 2014/142850; and U.S. Pat. Nos. 9,074,251, 8,829,171, each of which is incorporated herein by reference in its entirety. In some embodiments, an adaptor can be modified to prevent the formation of concatemers, for example by the addition of blocking groups that prevent extension of the adaptor at one or both ends. A blocking group is any chemical moiety that will block reaction of the compound to which it is attached during subsequent steps of the workflow, e.g., a moiety that will block activation of the adaptor by the ligase, reaction with a phosphate, and self-reaction. Examples of 3' blocking groups include a 3'-spacer C3, a dideoxynucleotide, and attachment to a substrate. Further examples of 3' blocking groups include an alkyl optionally substituted with one or more hydroxyl groups, a thiol, an azide, or an alkyne. In some aspects, blocking groups may provide functionalities that are useful in subsequent operations, such as enrichment, purification, further functionalization, and the like. Examples of 5' blocking groups include a dephosphorylated 5' nucleotide, and attachment to a substrate (e.g., where the blocking group is a substrate optionally attached via a linker).

Target nucleic acids include single-stranded nucleic acids and double-stranded nucleic acids. Methods to de-hybridize double-stranded nucleic acids to form single-stranded nucleic acids are well known in the art and include heat or chemical methods. Examples of target nucleic acids include DNA, such as genomic DNA or cDNA; RNA, such as mRNA, sRNA or rRNA; or a hybrid of DNA and RNA. A nucleic acid can contain phosphodiester bonds, and can include other types of backbones, comprising, for example, phosphoramide, phosphorothioate, phosphorodithioate, O-methylphosphoroamidite and peptide nucleic acid backbones and linkages. A nucleic acid can contain any combination of deoxyribo- and ribonucleotides, and any combination of bases, including uracil, adenine, thymine, cytosine, guanine, inosine, xanthanine, hypoxanthanine, isocytosine, isoguanine, and base analogs such as nitropyrrole (including 3-nitropyrrole) and nitroindole (including 5-nitroindole), etc. In some embodiments, a nucleic acid can include at least one promiscuous base. A promiscuous base can base-pair with more than one different type of base and can be useful, for example, when included in oligonucleotide primers or inserts that are used for random hybridization in complex nucleic acid samples such as genomic DNA samples. An example of a promiscuous base includes inosine that may pair with adenine, thymine, or cytosine. Other examples include hypoxanthine, 5-nitroindole, acylic 5-nitroindole, 4-nitropyrazole, 4-nitroimidazole and 3-nitropyrrole. Promiscuous bases that can base-pair with at least two, three, four or more types of bases can be used.

Target nucleic acids can include a sample in which the average size of a double-stranded nucleic acid in the sample is less than, greater than, or equal to about 2 kb, 1 kb, 500 bp, 400 bp, 200 bp, 100 bp, 50 bp, or a range between any two of the foregoing sizes. In some embodiments, the average size of a single-stranded nucleic acid in the sample is less than, greater than, or equal to about 2000 nucleotides, 1000 nucleotides, 500 nucleotides, 400 nucleotides, 200 nucleotides, 100 nucleotides, 50 nucleotides, or a range between any two of the foregoing sizes. A sample can include an amount of target nucleic acids less than, greater than, or equal to about 50 µg, 10 µg, 5 µg, 1 µg, 500 ng, 400 ng, 200 ng, 100 ng, 50 ng, 10 ng, or a range between any two of the foregoing amounts. Target nucleic acids can be obtained from low quality nucleic acid sources, such as a degraded sample such as a fixed sample and an ancient sample. Examples of fixed samples include those fixed with a compound such as formalin, glutaraldehyde, alcohol, osmic acid, and paraformaldehyde. The fixed sample can include a formalin-fixed paraffin-embedded (FFPE) sample. Ancient samples can include those having an age are greater than about 5 years, 10 years, 20 years, 50 years, 100 years, 500 years, 1000 years, or a range between any two of the foregoing ages.

Methods to dephosphorylate nucleic acids, such as the 5' nucleotide of a nucleic acid include contacting a nucleic acid with a phosphatase. Examples of phosphatases include calf intestinal phosphatase, shrimp alkaline phosphatase, antarctic phosphatase, and a heat-labile alkaline phosphatase (APEX™ phosphatase) (Epicentre, Madison, Wis.).

Methods to ligate single-stranded nucleic acids include contacting single-stranded nucleic acids with a ligase. Examples of single-stranded ligases include T4 RNA ligase 1, T4 RNA ligase 2, RtcB ligase, *Methanobacterium* RNA ligase, and TS2126 RNA ligase (CIRCLIGASE; Epicentre, Madison Wis.). Methods to ligate two nucleic acids together can be in a reaction volume in the presence of a volume excluding agent. As used herein, a "volume excluding agent" can include agents that reduce the effective volume in which a reaction, such as a ligation reaction, can occur. Examples of volume excluding agents include polymers, such as inert polymers, such as a polyethylene glycol (PEG), a neutral, highly branched, high-mass, hydrophilic polysaccharide (FICOLL), dextran, hetastarch, and polyvinylpyrrolidone. Examples of PEG useful with embodiments provided herein include PEG 600, PEG 800, PEG 1000, PEG 6000, and PEG 8000. The reaction volume can include a concentration, such as (weight/volume), of the volume excluding agent that is less than, greater than, or equal to about 5%, 10%, 20%, 30%, 40%, 50%, 60%, 70%, 80%, 90%, 95% or a range between any two of the foregoing percentages.

Methods to phosphorylate nucleic acids, such as the 5' nucleotide of a nucleic acid include contacting a nucleic acid with a kinase. Examples of kinases include T4 polynucleotide kinase.

Some embodiments provided herein can be performed in a single reaction volume. In some embodiments, a method of preparing a nucleic acid can be performed within a reduced period of time, such as within a period less than about 12 hours, a period less than about 6 hours, or a period less than about 3 hours.

An embodiment is depicted in FIG. 1 in which a target double-stranded DNA fragment is dephosphorylated and denatured to form a target single-stranded DNA. A first 64 bp adaptor that includes a phosphorylated 5' end, a P7' sequence, and a blocked 3' end, is ligated to the 3' end of the target single-stranded DNA to form a ligated DNA with a ligase, such as TS2126 RNA ligase (CIRCLIGASE™) (Lucigen Corporation, Middleton, Wis.). The 5' end of ligated DNA is phosphorylated with a kinase, such as T4 polynucleotide kinase. A second 60 bp adaptor that includes a P5 sequence is ligated to the 5' of the phosphorylated ligated DNA to form a member (5'-P5-ssDNA insert-P7-3') of a DNA library. Example primer sequences can include: a P5 primer sequence (SEQ ID NO:01: aatgatacggcgaccaccga); a P5' primer sequence (SEQ ID NO:02: tcggtggtcgccgtatcatt); a P7 primer sequence (SEQ ID NO:03: caagcagaagacggcatacga); and a P7' primer sequence (SEQ ID NO:04: tcgtatgccgtcttctgcttg).

In some embodiments, a method of preparing a library of nucleic acids can include dephosphorylating the 5' ends of target single-stranded nucleic acids to prevent the formation of concatemers in subsequent ligation steps; ligating first adaptors to the 3' ends of the dephosphorylated targets using a single-stranded ligase, in which the 3' ends of the first adaptors are blocked; re-phosphorylating of the 5' ends of the ligated targets; ligating a second adaptor to the 5' ends of the dephosphorylated targets using the single-stranded ligase, in which the 5' ends of the second adaptors are non-phosphorylated, thereby obtaining a library of nucleic acids. In some embodiments, the second adaptor is attached to a substrate. In some embodiments, the substrate comprises a bead.

Some embodiments include removing non-ligated single-stranded first adaptors before ligating a second adaptor to the 5' ends of the dephosphorylated targets. In some embodiments, the non-ligated single-stranded first adaptors can be hybridized to a capture probe. In some embodiments, the capture probe comprises a sequence complementary to at least a portion of the first adaptor. In some such embodiments, hybridization to a capture probe inhibits the ligation of the non-ligated first adaptors to single-stranded second adaptors. In some embodiments, the 3' end of the capture probe comprises a blocking group. In some embodiments, the 5' end of the capture probe comprises a blocking group. In some embodiments, the non-ligated single-stranded first adaptors can be removed by digestion. In some embodiments, digesting the non-ligated single-stranded first adaptors comprises contacting the non-ligated single-stranded first adaptors with a 5'-phophate-dependent exonuclease, and optionally also a 5'-deadenylase.

Another embodiment is depicted in FIG. 2 in which a double-stranded target nucleic acid is partially digested with a 5' exonuclease to form a double-stranded nucleic acid with single-stranded 3' overhangs. A first 64 bp adaptor that includes a phosphorylated 5' end, a P7' sequence, and a blocked 3' end, is ligated to the 3' ends of the target double-stranded DNA to form a ligated DNA with a ligase, such as TS2126 RNA ligase (CIRCLIGASE™). The ligated DNA is dehybridized to form single-stranded nucleic acids. A second 60 bp adaptor that includes a P5 sequence is ligated to the 5' of the phosphorylated ligated DNA to form a member (5'-PS-ssDNA insert-P7-3') of a DNA library.

In some embodiments, a method of preparing a library of nucleic acids can include contacting target double-stranded nucleic acids with a 5' exonuclease to obtain a plurality of modified double-stranded nucleic acids with single-stranded 3' overhangs; ligating a first adaptor to the 3' ends of the modified double-stranded nucleic acids in the presence of a ligase and a volume excluding agent, wherein the 3' end of the first adaptor comprises a blocking group; dehybridizing the modified double-stranded nucleic acids ligated to the first adaptors to obtain a plurality of single-stranded nucleic acids; and ligating a second adaptor to the 5' ends of the single-stranded nucleic acids in the presence of the ligase, thereby obtaining a library of nucleic acids.

An embodiment is depicted in FIG. 3 in which a target single-stranded DNA is dephosphorylated with an alkaline phosphatase. A first adaptor that includes a phosphorylated 5' end, a P5' sequence, and a blocked 3' end, is ligated to the 3' end of the target single-stranded DNA to form a ligated DNA with a ligase, such as TS2126 RNA ligase (CIRCLIGASE'). The ligated DNA is hybridized via the first adaptor to a capture probe containing a P5 sequence and is attached to a bead. The capture probe is extended to form an extended DNA, and the ligated DNA is removed from the extended DNA. A second adaptor that includes a phosphorylated 5' end, a P7' sequence, and a blocked 3' end, is ligated to the 3' end of the extended DNA with a ligase, such as TS2126 RNA ligase (CIRCLIGASE™), to form a member (P5-Insert'-P7') of a DNA library attached to a bead.

Figure 26:
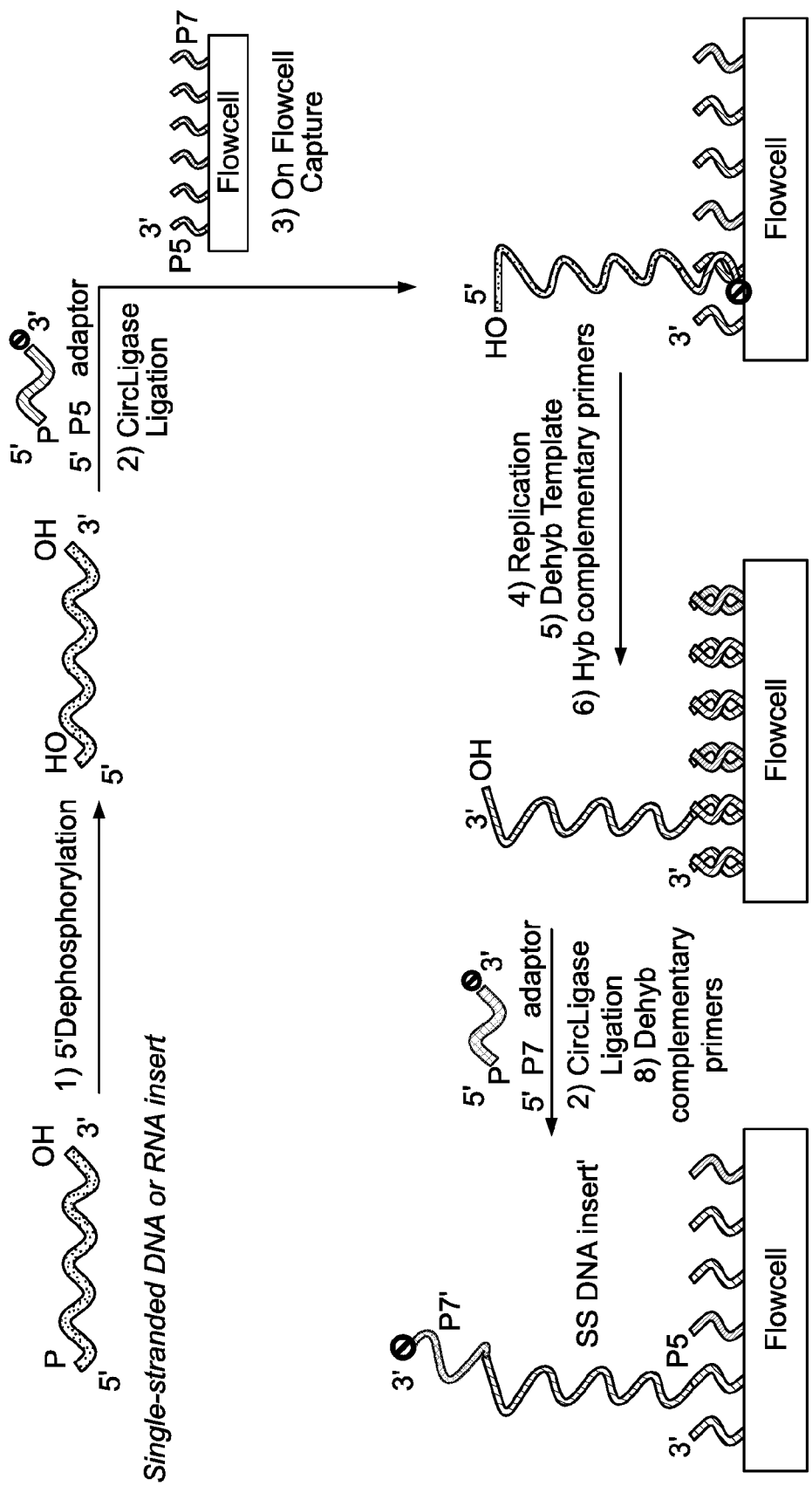
FIG. 26 depicts a schematic outline for a method to prepare a library of single-stranded nucleic acids according to one embodiment. A library can be prepared by dephosphorylating the 5' end of a single-stranded nucleic acid, ligating using TS2126 RNA ligase (CIRCLIGASE™) a P5' adaptor containing a 3' blocking group to the 3' end of the single-stranded nucleic acid, hybridizing the first ligation product to a P5 capture probe attached to a flow cell, extending the capture probe, removing the hybridized first ligation product from the extended capture probe, hybridizing complementary primers, ligating a P7' adaptor containing a 3' blocking group to the 3' end of the extended capture probe, and dehybridizing the complementary primers.

In some embodiments, a method of preparing a library of nucleic acids can include dephosphorylating the 5' ends of target single-stranded nucleic acids; ligating a first adaptor to the 3' ends of the single-stranded nucleic acids in the presence of a ligase and a volume excluding agent, wherein the 3' end of the first adaptor comprises a blocking group; hybridizing the ligated first adaptor with a capture probe; extending the capture probe, and ligating a second adaptor to the 3' end of the extended capture probe in the presence of the ligase, wherein the 3' end of the second adaptor comprises a blocking group, thereby obtaining a library of nucleic acids. Some embodiments also include removing the hybridized ligated first adaptor from the extended capture probe. In some embodiments, the capture probe is attached to a substrate. In some embodiments, the substrate with the capture probe is a flow cell, a bead, glass, controlled pore glass, plastic, silicon, fused silica, silicon dioxide, silicon nitride, silicon derivatives, gallium arsenide, indium phosphide, aluminum, ceramics, polyimide, quartz, resins, or a polymer or co-polymer (such as polystyrene). Substrates may be composed of layers of multiple materials, or mixture of materials. Substrates may be rigid or semi-rigid. Substrates may be flat, round, or textured. In some embodiments, substrates may be a rigid material such as glass and/or silica derivatives with one or more polymer materials coated thereon. In some embodiments, the substrate comprises a bead. In some embodiments, the capture probe comprises a capture probe index. In some embodiments, the capture probe index is indicative of the source of a capture probe. In some embodiments, the capture probe comprises a cleavable linker. Some embodiments also include cleaving the cleavable linker. In some embodiments, the capture probe is attached to a substrate, such as a flow cell (see FIG. 26), and the extending then takes place on the substrate. Where the substrate is a flow cell, the resulting library may be sequenced directly. In some embodiments, the method further comprises hybridizing complementary primers to the extended capture probe, ligating a P7' adaptor containing a 3' blocking group to the 3' end of the extended capture probe, and dehybridizing the complementary primers, as shown, for example, in FIG. 26.

Figure 4B:
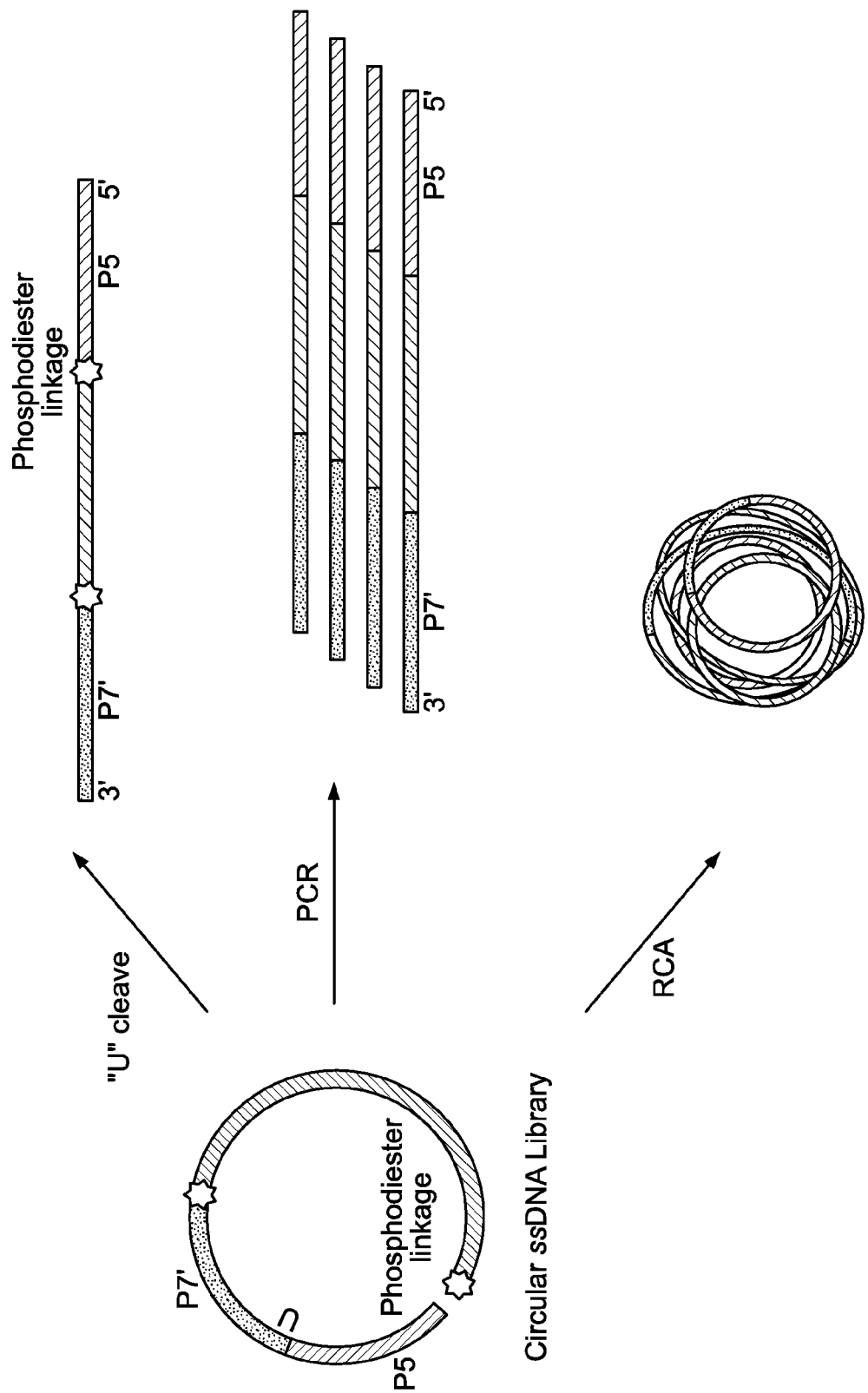
FIG. 4B is a schematic outline in which the circular nucleic acid of FIG. 4B can be linearized by cleaving a cleavable site ("U"), or amplified by PCR, or by rolling circle amplification (RCA).

An embodiment is depicted in FIG. 4A in which in which a target double-stranded DNA fragment is dephosphorylated and denatured to form a target single-stranded DNA. An adaptor that includes, 5' to 3': a phosphorylated 5' end, a P7' sequence, a cleavable site ("U"), a P5 sequence and a blocked 3' end ("R"), is provided. The adaptor is ligated with a ligase, to the 3' end of the target single-stranded DNA to form a ligated DNA. The 5' end of ligated DNA is phosphorylated with a kinase. The blocked 3' end of the ligated DNA is deprotected, and the ligated DNA is circularized by ligation with a ligase to form a member of a library comprising circular single-stranded DNA. In some embodiments, a circular nucleic acid can be used to generate single-stranded nucleic acids by any one of a variety of techniques. Some example embodiments are depicted in FIG. 4B in which the circular nucleic acid can be linearized by cleaving the cleavable site that can includes an uracil residue. The circular nucleic acid can also be used to generate single-stranded nucleic acids by amplification, such as PCR, using primer sites within the adaptor. The circular nucleic acid can also be amplified by rolling circle amplification (RCA).

In some embodiments, a method of preparing a library of nucleic acids can include: dephosphorylating the 5' ends of target single-stranded nucleic acids; ligating a linker to the 3' ends of the single-stranded nucleic acids, wherein the linker comprises a first adaptor and a second adaptor, and the 3' end of the linker comprises a blocking group; phosphorylating the 5' ends of the ligated single-stranded nucleic acids; deprotecting the 3' ends of the phosphorylated nucleic acids, and circularizing the deprotected nucleic acids by ligation, thereby obtaining a library of circular nucleic acids.

In some embodiments, the linker comprises a cleavable site between the first adaptor and the second adaptor. In some such embodiments, cleavage of the cleavable site of a circular nucleic acid can result in a linear nucleic acid having the first adaptor at one end, and the second adaptor at the other end of the linear nucleic acid. In some embodiments, cleavable sites include restriction sites, sites comprising at least one uracil residue, and sites containing atypical bases, such as 8-oxoguanine and dithiol groups. Some embodiments include linearizing the circular nucleic acids by cleavage at the cleavable site. Examples of cleaving the cleavable site include contacting the site with an uracil-specific excision reagent, such as an enzyme selected from uracil DNA glycosylase (UDG) and DNA glycosylase-lyase endonuclease VIII, or mixture thereof, or contacting the site with a restriction endonuclease.

Some embodiments also include amplifying the circular nucleic acids by comprising hybridizing primers to the first and second adaptors. Examples of methods of amplification include PCR, rolling circle amplification (RCA), and cluster amplification. In some such embodiments, amplification by RCA can be performed in solution, or circular single-stranded nucleic acids can be captured on a surface, such as the surface of a flow cell, and amplified. In some embodiments, the amplification comprises contacting the circular nucleic acids with a polymerase that forms a linear product on contacting an uracil residue in a template. Example polymerases include a *Pyrococcus*-like proofreading polymerase, such as a PHUSION DNA polymerase.

Some embodiments include a method of preparing a single-stranded nucleic acid library, comprising: (a) obtaining a plurality of single-stranded nucleic acids; (b) contacting the single-stranded nucleic acids with a heat-labile alkaline phosphatase (APEX™ phosphatase), thereby dephosphorylating the 5' ends of the single-stranded nucleic acids; (c) ligating a first adaptor to the 3' ends of the single-stranded nucleic acids in a reaction volume comprising TS2126 RNA ligase (Lucigen Corporation, Middleton, Wis.) and at least 45% (w/v) polyethylene glycol (PEG), wherein the 3' end of the first adaptor comprises a 3'-spacer C3 blocking group; (d) contacting the ligated single-stranded nucleic acids with T4 polynucleotide kinase, thereby phosphorylating the 5' ends of the ligated single-stranded nucleic acids; and (e) ligating a second adaptor to the 5' ends of the phosphorylated ligated single-stranded nucleic acids in the presence of the ligase and PEG, wherein the 5' end of the second adaptor is non-phosphorylated, thereby obtaining a library of nucleic acids.

Some embodiments include a method of preparing a single-stranded nucleic acid library, comprising: (a) obtaining a plurality of double-stranded nucleic acids; (b) contacting the double-stranded nucleic acids with a 5' exonuclease to obtain a plurality of modified double-stranded nucleic acids with single-stranded 3' overhangs; (c) ligating a first adaptor to the 3' ends of the modified double-stranded nucleic acids in a reaction volume comprising TS2126 RNA ligase and at least 45% (w/v) polyethylene glycol (PEG), wherein the 3' end of the first adaptor comprises a 3'-spacer C3 blocking group; (d) dehybridizing the modified double-stranded nucleic acids ligated to the first adaptors to obtain a plurality of single-stranded nucleic acids; and (e) ligating a second adaptor to the 5' ends of the single-stranded nucleic acids in the presence of the ligase and PEG, wherein the 5' end of the second adaptor is non-phosphorylated, thereby obtaining a library of nucleic acids.

Some embodiments include a method of preparing a single-stranded nucleic acid library, comprising: (a) obtaining a plurality of single-stranded nucleic acids; (b) contacting the single-stranded nucleic acids with a heat-labile alkaline phosphatase (APEX™ phosphatase), thereby dephosphorylating the 5' ends of the single-stranded nucleic acids; (c) ligating a first adaptor to the 3' ends of the single-stranded nucleic acids in a reaction volume comprising TS2126 RNA ligase and at least 45% (w/v) polyethylene glycol (PEG), wherein the 3' end of the first adaptor comprises a 3'-spacer C3 blocking group; (d) contacting the ligated single-stranded nucleic acids with T4 polynucleotide kinase, thereby phosphorylating the 5' ends of the ligated single-stranded nucleic acids; (e) removing non-ligated single-stranded first adaptors from the ligated single-stranded nucleic acids by hybridizing the single-stranded first adaptors with a capture probe, wherein the capture probe comprises: a 3' end comprising a 3'-spacer C3 blocking group, a non-phosphorylated 5' end, and a sequence complementary to at least a portion of the first adaptor; and (f) ligating a second adaptor to the 5' ends of the phosphorylated ligated single-stranded nucleic acids in the presence of the ligase and PEG, wherein the 5' end of the second adaptor is non-phosphorylated, thereby obtaining a library of nucleic acids.

Some embodiments include a method of preparing a nucleic acid library attached to beads, comprising: (a) obtaining a plurality of single-stranded nucleic acids; (b) contacting the single-stranded nucleic acids with a heat-labile alkaline phosphatase (APEX™ phosphatase), thereby dephosphorylating the 5' ends of the single-stranded nucleic acids; (c) ligating a first adaptor to the 3' ends of the single-stranded nucleic acids in a reaction volume comprising TS2126 RNA ligase and at least 45% (w/v) polyethylene glycol (PEG), wherein the 3' end of the first adaptor comprises a 3'-spacer C3 blocking group; (d) hybridizing the ligated first adaptor with a capture probe, wherein the capture probe is attached to a bead; (e) extending the capture probe; and (f) ligating a second adaptor to the 3' end of the extended capture probe in the presence of the ligase and PEG, wherein the 5' end of the second adaptor is non-phosphorylated, thereby obtaining a library of nucleic acids.

Some embodiments include a method of preparing an indexed nucleic acid library, comprising: (a) obtaining: a plurality of first single-stranded nucleic acids comprising a first index, wherein the 5' ends of the first single-stranded nucleic acids are attached to a plurality of beads, and a plurality of second single-stranded nucleic acids comprising a second index and a capture probe, wherein the 3' ends of the second single-stranded nucleic acids comprise a 3'-spacer C3 blocking group; (b) ligating the 3' ends of the first single-stranded nucleic acids to the 5' ends of the second single-stranded nucleic acids in a reaction volume comprising TS2126 RNA ligase and at least 45% (w/v) polyethylene glycol (PEG); (c) hybridizing a target nucleic acid to the capture probe; and (d) extending the target nucleic acid, thereby obtaining a library of indexed nucleic acids.

Removing Non-Ligated Single-Stranded Adaptors

Some embodiments of the systems, methods and compositions provided herein include removing single-stranded non-ligated adaptors from ligated adaptors, such as adaptors ligated to single-stranded nucleic acids. In some embodiments, removal of single-stranded non-ligated adaptors from ligated adaptors can increase the efficiency of amplifying a prepared nucleic acid library, such as reducing the likelihood or amount of primer-dimer formation in subsequent amplification steps.

Figure 5:
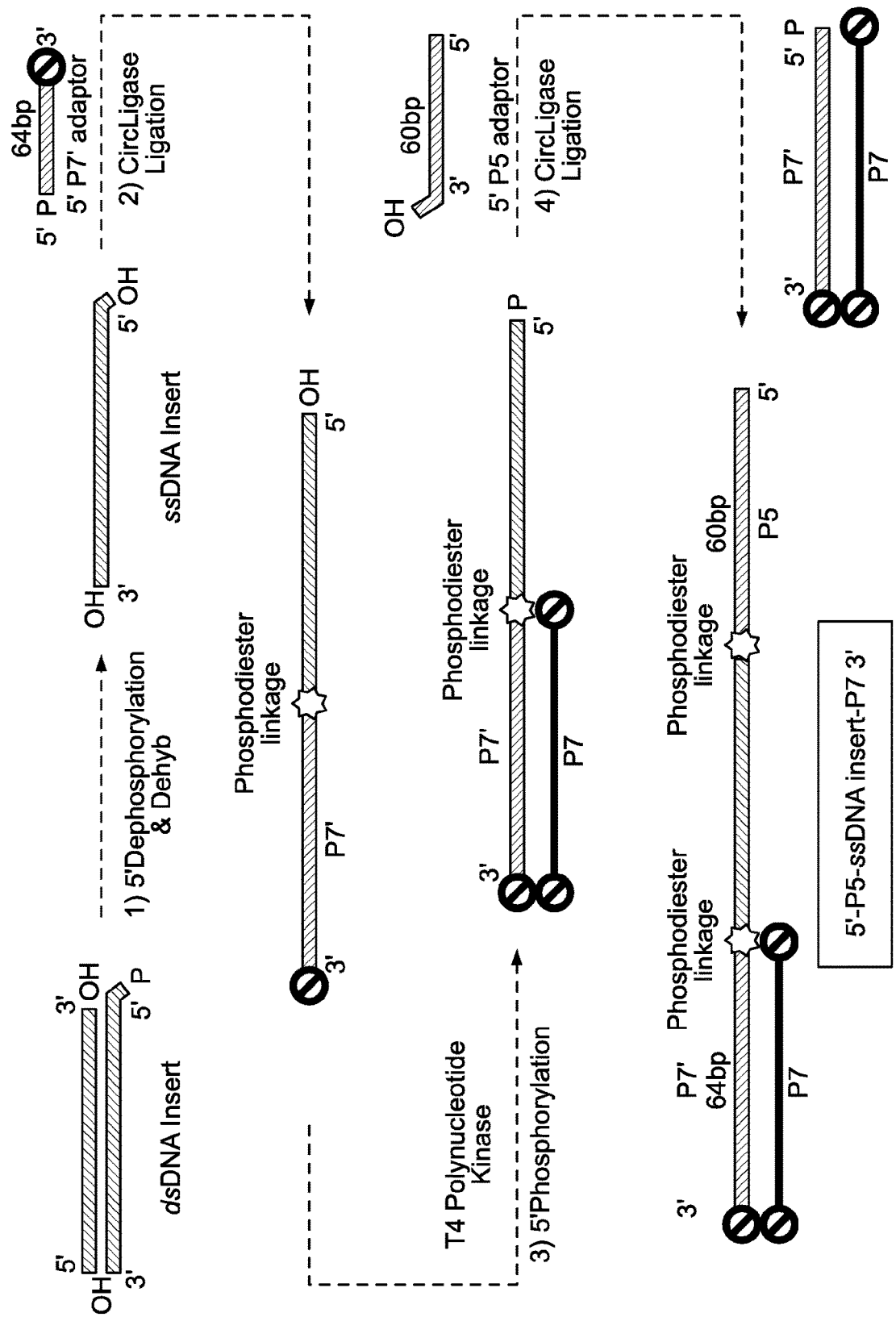
FIG. 5 is a schematic outline for a method to prepare a library of single-stranded nucleic acids that includes the embodiment shown in FIG. 1.

Some embodiments include systems or methods to remove single-stranded non-ligated adaptors and can include hybridizing the single-stranded non-ligated adaptors with a capture probe. An embodiment is depicted in FIG. 5 in which a target double-stranded DNA fragment is dephosphorylated and denatured to form a target single-stranded DNA. A first 64 bp adaptor that includes a phosphorylated 5' end, a P7' sequence, and a blocked 3' end, is ligated with a ligase, to the 3' end of the target single-stranded DNA to form a ligated DNA. The 5' end of ligated DNA is phosphorylated with a kinase, such as T4 polynucleotide kinase. Non-ligated first adaptors are removed from the ligated DNA by hybridization to a capture probe containing a P7 sequence. A second 60 bp adaptor that includes a P5 sequence is ligated to the 5' of the phosphorylated ligated DNA to form a member (5'-PS-ssDNA insert-P7-3') of a DNA library. In some such embodiments, hybridization to a capture probe can inhibit the ligation of the non-ligated first adaptors to the single-stranded second adaptors. In some embodiments the capture probe can include the complement of at least a portion of the single-stranded non-ligated adaptor. In some embodiments, the capture probe can include a 3' and/or a 5' blocking group to prevent formation of concatemers. In some embodiments, the capture probe can be attached to a substrate, such as a bead.

Figure 6:
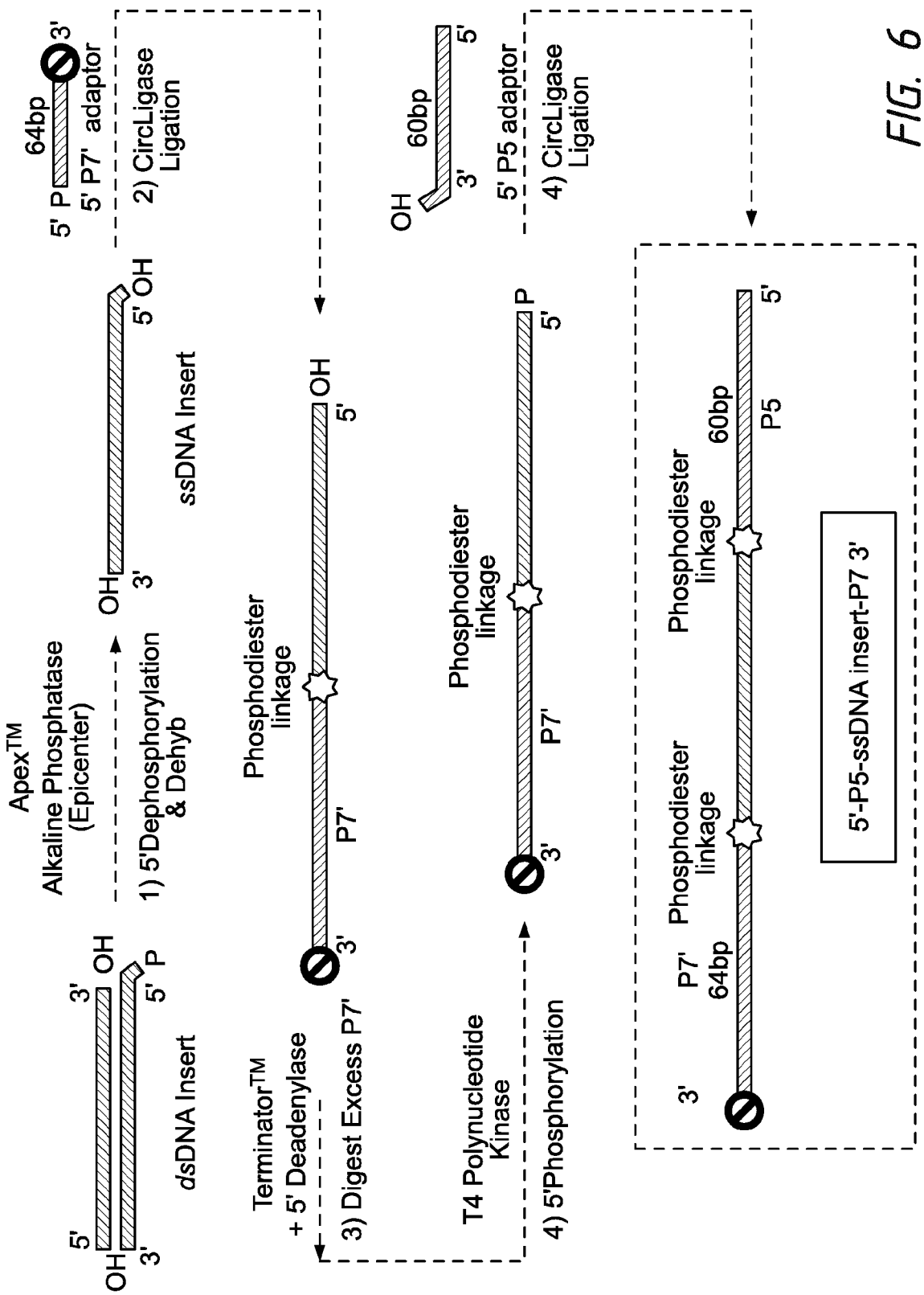
FIG. 6 is a schematic outline for a method to prepare a library of single-stranded nucleic acids according to one embodiment. A double-stranded nucleic acid is dehybridized to form a single-stranded nucleic acid, and a library can be prepared by dephosphorylating using a heat-labile alkaline phosphatase (APEX™ phosphatase) the 5' end of the single-stranded nucleic acid, ligating using TS2126 RNA ligase (CIRCLIGASE™) a P7' adaptor containing a 3' blocking group to the 3' end of the single-stranded nucleic acid, removing excess non-ligated single-stranded P7' adaptors by digesting with a 5' phosphate-dependent exonuclease (TERMINATOR™ 5' phosphate-dependent exonuclease) and 5' deadenylase, re-phosphorylating the 5' end of a ligated single-stranded nucleic acid, and ligating a P5 adaptor containing a non-phosphorylated 5' end to the 5' end of a ligated single-stranded nucleic acid.

Some embodiments to remove single-stranded non-ligated adaptors can include digesting the single-stranded non-ligated adaptors. Some such embodiments can include contacting the single-stranded non-ligated adaptors with a nuclease, such as a 5'-phosphate-dependent exonuclease, such as TERMINATOR™ 5'-phosphate-dependent exonuclease (Epicentre, Madison, Wis.). An embodiment is depicted in FIG. 6 in which a target double-stranded DNA fragment is dephosphorylated and denatured to form a target single-stranded DNA. A first 64 bp adaptor that includes a phosphorylated 5' end, a P7' sequence, and a blocked 3' end, is ligated with a ligase to the 3' end of the target single-stranded DNA to form a ligated DNA. Non-ligated first adaptors are removed by digestion with a 5'-phosphate-dependent exonuclease and a 5' deadenylase. The 5' end of ligated DNA is phosphorylated with a kinase, such as T4 polynucleotide kinase. A second 60 bp adaptor that includes a P5 sequence is ligated to the 5' of the phosphorylated ligated DNA to form a member (5'-PS-ssDNA insert-P7-3') of a DNA library.

Some embodiments to remove single-stranded non-ligated adaptors can include the use of beads. Advantageously, the use of beads can include washing components of a reaction from the beads and components attached to the beads. In some embodiments, a first adaptor can be ligated to the 3' ends of dephosphorylated single-stranded nucleic acids. The first adaptor can include a 3' blocking group, and can include target sequences. The target sequences can be hybridized to capture probes attached to a substrate. In some embodiments, the substrate can include a bead. The capture probe can include sequencing primer sites, indexes, and amplification primer sites. Single-stranded non-ligated adaptors can be washed from the substrate and the hybridized ligated single-stranded nucleic acids. The capture probe can be extended. In some embodiments, the hybridized ligated single-stranded nucleic acids can be removed from the extended capture probe. A second adaptor can be ligated to the 5' ends of the extended capture probes. In some embodiments, the second adaptors include a blocking group at the 3' ends. The second adaptor can include sequencing primer sites, indexes, and amplification primer sites.

Preparing Indexed Libraries

Some embodiments of the systems, methods and compositions provided herein include methods of preparing an indexed nucleic acid library. Adaptors and/or capture probes can include indexes. Examples of the use and preparation of indexes useful with embodiments provided herein can be found in Int. Pub. Nos. WO 2012/061832 and WO 2014/142850; and U.S. Pat. Nos. 9,074,251, 8,829,171, each of which is incorporated herein by reference in its entirety. In some embodiments an index can be incorporated into a target nucleic acid by ligation. In some embodiments, an index can be incorporated into to a nucleic acid by extension of a capture probe, adaptor or target nucleic acid. Thus, indexed libraries can be readily prepared by methods provided herein.

In some embodiments, a population of capture probes can be prepared. In some embodiments, a capture probe can be prepared by ligating a first adaptor to a second adaptor. The adaptors can each include an index. The first adaptor can be attached to a substrate, such as a bead. The second adaptor can include a hybridization probe. The hybridization probe can hybridize to target single-stranded nucleic acids. Target single-stranded nucleic acids can hybridize to the hybridization probe, and be extended, thereby incorporating sequences complementary to the index of one or more of the adaptors.

Some embodiments can include obtaining a plurality of first adaptors comprising a first index, wherein the 5' ends of the first adaptors comprise a 5' blocking group, and a plurality of second adaptors comprising a second index and a capture probe, wherein the 3' ends of the second adaptors comprise a 3' blocking group. Some embodiments also include ligating the 3' ends of the first single-stranded nucleic acids to the 5' ends of the second single-stranded nucleic acids in the presence of a ligase. Some embodiments also include hybridizing a target nucleic acid to the capture probe. Some embodiments also include extending the target nucleic acid, thereby obtaining a library of indexed nucleic acids. Some embodiments also include amplifying the extended target nucleic acids. In some embodiments, the 5' blocking group comprises a dephosphorylated nucleotide, or an attachment to a substrate. In some embodiments, the substrate comprises a plurality of beads.

Kits, Reaction Vessels and Flow Cells

Embodiments of the systems and methods provided herein include kits, reaction vessels, and flow cells containing any one or more of the components useful to prepare nucleic acid libraries by ligation of adaptors to nucleic acids, such as single-stranded nucleic acids and/or double-stranded nucleic acids. Example components include a first adaptor wherein the 3' end of the first adaptor comprises a blocking group, a ligase, a volume excluding agent, a dephosphorylating agent, a second adaptor in which the 5' end of the second adaptor comprises a blocking group, sequencing primers, amplification primers, nucleic acids comprising indexes, and 5' exonucleases. In some embodiments, a kit can include a reagent for any method provided herein. In some embodiments, a kit can include a reaction vessel. In some embodiments, a kit can include a flow cell comprising the reaction vessel.

Some embodiments include a reaction vessel comprising a reaction volume in which a method provided herein can be performed. In some such embodiments, a reaction vessel can include components of any stage or step of a method provided herein. In some embodiments, a reaction vessel can include a plurality of nucleic acids, such as single-stranded nucleic acids and/or double-stranded nucleic acids; a first adaptor wherein the 3' end of the first adaptor comprises a blocking group; a ligase; and a volume excluding agent. In some embodiments, a reaction vessel can also include a second adaptor. In some embodiments, a reaction vessel can also include a dephosphorylating agent.

In some embodiments, a reaction vessel can include a reaction volume. In some embodiments, the reaction volume can include a plurality of nucleic acids, such as single-stranded nucleic acids and/or double-stranded nucleic acids; a first adaptor wherein the 3' end of the first adaptor comprises a blocking group; a second adaptor; a dephosphorylating agent; a ligase; and a volume excluding agent.

In some embodiments, a reaction volume can include a plurality of first single-stranded nucleic acids comprising a first index, wherein the 5' ends of the first single-stranded nucleic acids comprise a 5' blocking group, a plurality of second single-stranded nucleic acids comprising a second index and a capture probe, wherein the 3' ends of the second single-stranded nucleic acids comprise a 3' blocking group; and a ligase.

In some embodiments, the first adaptor is ligated to the 3' ends of the plurality of single-stranded nucleic acids, thereby forming a plurality of modified single-stranded nucleic acids. In some embodiments, a non-ligated first adaptor is hybridized to a capture probe. In some embodiments, the capture probe comprises a sequence complementary to at least a portion of the first adaptor.

In some embodiments, the 5' end of the second adaptor is non-phosphorylated. In some embodiments, the second adaptor is ligated to the 5' ends of the plurality of modified single-stranded nucleic acids. In some embodiments, the dephosphorylating agent comprises a phosphatase. In some embodiments, the phosphatase is inactivated. Examples of phosphatases include calf intestinal phosphatase, shrimp alkaline phosphatase, antarctic phosphatase, and a heat-labile alkaline phosphatase (APEX™ phosphatase).

In some embodiments, the first adaptor and/or second adaptor can include a sequencing primer binding site. Examples of sequencing binding sites include a P7 sequence, complement, or reverse complement thereof; and a P5 sequence, complement, or reverse complement thereof.

In some embodiments, the first adaptor and/or second adaptor can include an adaptor index. In some embodiments, the first adaptor index is different from the second adaptor index. In some embodiments, the adaptor index is indicative of the source of the plurality of single-stranded nucleic acids.

Some embodiments provided herein include a reaction vessel comprising a reaction volume comprising: a plurality of first single-stranded nucleic acids comprising a first index, wherein the 5' ends of the first single-stranded nucleic acids comprise a 5' blocking group; a plurality of second single-stranded nucleic acids comprising a second index and a capture probe, wherein the 3' ends of the second single-stranded nucleic acids comprise a 3' blocking group; and a ligase.

In some embodiments, a blocking group comprises a 3'-spacer C3, a dideoxynucleotide, or a phosphate group. In some embodiments, a blocking group can include attachment to a substrate. Examples of a substrate include beads.

In some embodiments, the volume excluding agent is selected from the group consisting of a polyethylene glycol (PEG), dextran, hetastarch, a neutral, highly branched, high-mass, hydrophilic polysaccharide (FICOLL), and polyvinylpyrrolidone. Examples of PEG useful with embodiments provided herein include PEG 600, PEG 800, PEG 1000, PEG 6000, and PEG 8000. The reaction volume can include a concentration, such as (weight/volume), of the volume excluding agent that is less than, greater than, or equal to about 5%, 10%, 20%, 30%, 40%, 50%, 60%, 70%, 80%, 90%, 95% or a range between any two of the foregoing percentages.

In some embodiments, the ligase comprises a single-stranded nucleic acid ligase. Examples of single-stranded nucleic acid ligase include T4 RNA ligase 1, T4 RNA ligase 2, RtcB ligase, *Methanobacterium* RNA ligase, and TS2126 RNA ligase (CIRCLIGASE).

Some embodiments provided herein include a flow cell comprising a reaction vessel provided herein. Some embodiments include a system including a reaction vessel provided herein and a detector for obtaining sequencing data.

A flow cell can include a chamber having a surface across which one or more fluid reagents can be flowed. Generally, a flow cell will have an ingress opening and an egress opening to facilitate flow of fluid. Examples of flow cells and related fluidic systems and detection platforms that can be readily used in the methods of the present disclosure are described, for example, in Bentley et al., Nature 456:53-59 (2008), WO 04/018497; U.S. Pat. No. 7,057,026; WO 91/06678; WO 071123744; U.S. Pat. Nos. 7,329,492; 7,211,414; 7,315,019; 7,405,281, and US 2008/0108082, each of which is incorporated herein by reference in its entirety.

EXAMPLES

Example 1—Ligation of Adaptors to Single-Stranded Target Nucleic Acids

A four-step single-stranded DNA (ssDNA) library preparation method was performed using a single-stranded DNA as the target nucleic acid. FIG. 1 provides an overview of the four steps which included 5' dephosphorylation of the target nucleic acid; ligation of a 3' adaptor to the 3' end of the target nucleic acid, in which the 3' end of the 3' adaptor is blocked to inhibit self-concatemerization; re-phosphorylation of the 5' dephosphorylation of the ligated target nucleic acid; and ligation of a 5' adaptor to the 5' end of the ligated target nucleic acid, in which the 5' end of the 5' adaptor is blocked to inhibit self-concatemerization.

Figure 7:
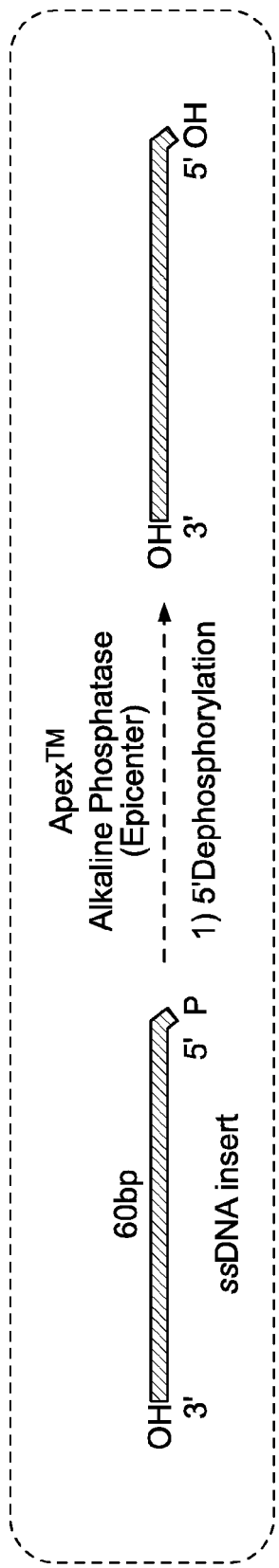
FIG. 7 depicts the results of an experiment to dephosphorylate the 5' end of a 60-mer single-stranded nucleic acid (3'OH-60-Phos 5') and confirm that the products (3'OH-60-OH 5') cannot form concatemers. The top panel is a schematic showing the dephosphorylation using a heat-labile alkaline phosphatase (APEX™ phosphatase). The table outlines conditions for reactions performed and run on the gel shown in the lower panel including TS2126 RNA ligase (CIRCLIGASE™).
Figure 7:
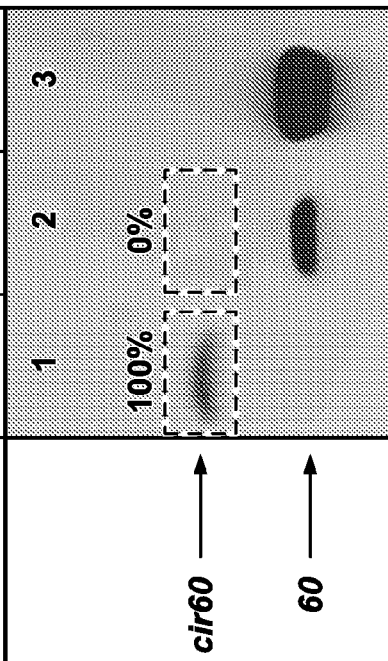

To examine the dephosphorylation step, the 5' end of a 60-mer single-stranded nucleic acid (3'OH-60-Phos 5') was dephosphorylated using a heat-labile alkaline phosphatase (APEX™ phosphatase) (Epicentre, Madison, Wis.) in a reaction volume with 25% polyethylene glycol (PEG). The degree of 5' dephosphorylation was assayed using a single-strand ligase, TS2126 RNA ligase (CIRCLIGASE™) (Lucigen Corporation, Middleton, Wis.) to confirm that dephosphorylated products did not form concatemers. As depicted in FIG. 7, the dephosphorylation efficiency of the alkaline phosphatase was about 100%.

Figure 8:
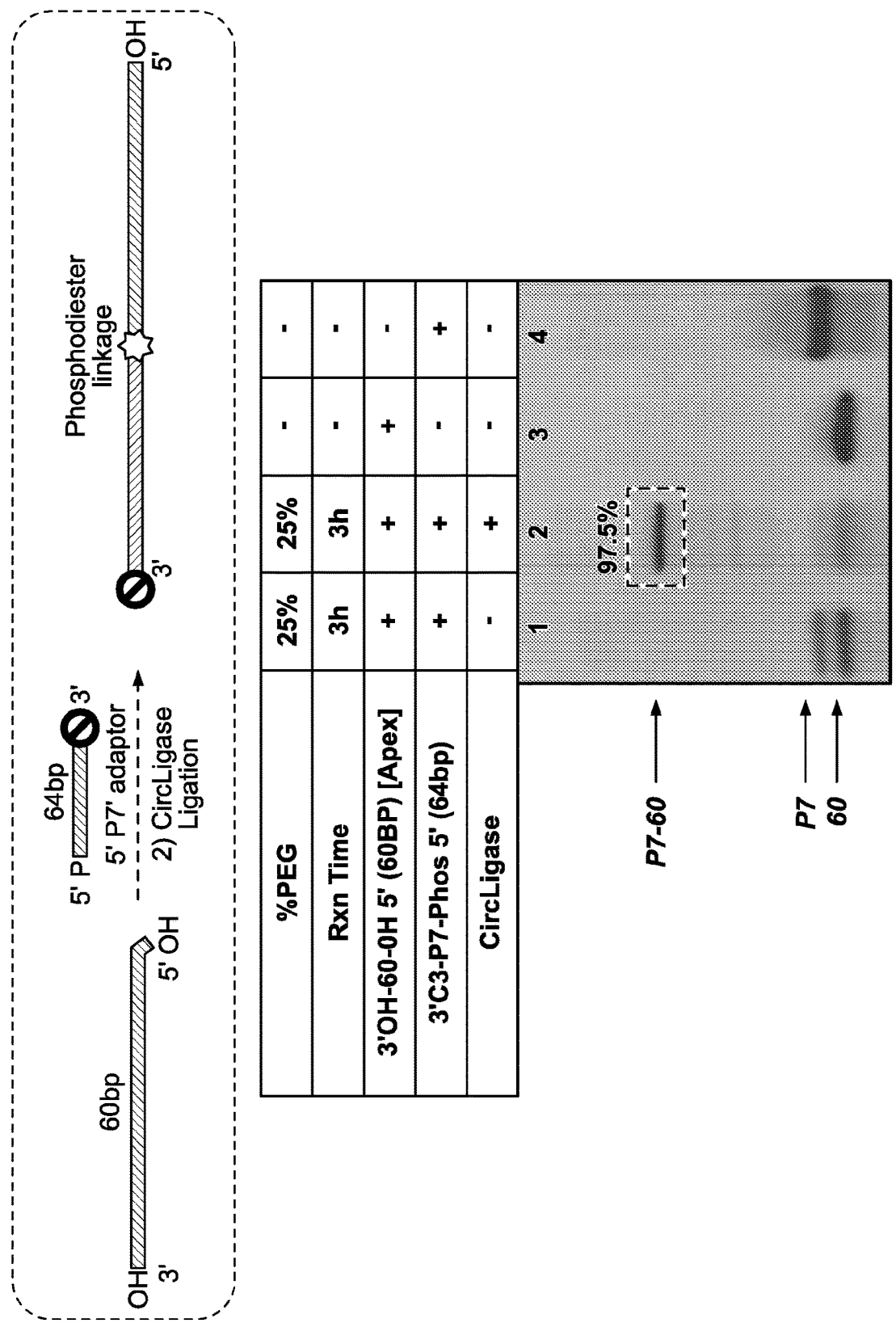
FIG. 8 depicts the results of an experiment to ligate a 64-mer P7' adaptor (3'C3-P7-phos 5') containing a 3' blocking group to the 3' end of a dephosphorylated 60-mer single-stranded nucleic acid (3'OH-60-OH 5'). The top panel is a schematic showing the ligation using TS2126 RNA ligase (CIRCLIGASE™). The table outlines conditions for reactions performed and run on the gel shown in the lower panel.

To examine the initial ligation step, a 64-mer P7' adaptor (3'C3-P7-phos 5') containing a 3' blocking group was ligated to the 3' end of a dephosphorylated 60-mer single-stranded nucleic acid (3'OH-60-OH 5') using TS2126 RNA ligase (CIRCLIGASE™) in a reaction volume containing 25% PEG. The 3' end of the P7' adaptor was blocked to inhibit self-concatemerization. As shown in FIG. 8, the yield for this ligation step (Lane 2) was determined to be 97.5%.

Figure 9:
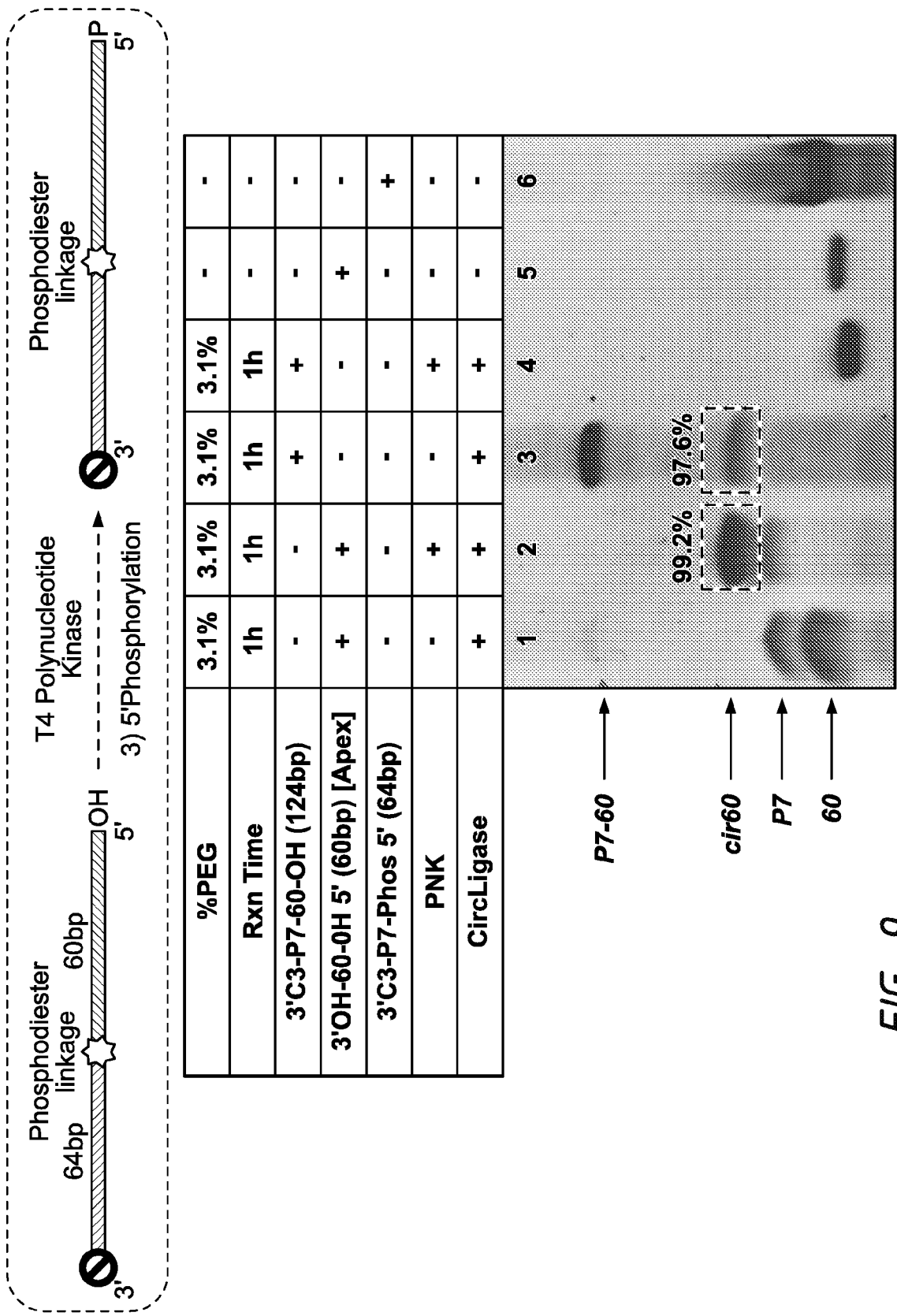
FIG. 9 depicts the results of an experiment to re-phosphorylate the 5' end of a 124-mer dephosphorylated single-stranded nucleic acid containing a ligated 64-mer adaptor with a 3' blocking group (3'C3-P7-60-OH). The top panel is a schematic showing the kinase reaction. The table outlines conditions for reactions performed and run on the gel shown in the lower panel including TS2126 RNA ligase (CIRCLIGASE™).

To examine the kinase step, the 5' end of a 124-mer dephosphorylated single-stranded nucleic acid containing a ligated 64-mer adaptor with a 3' blocking group (3'C3-P7-60-OH) was re-dephosphorylated using T4 polynucleotide kinase (PNK). As depicted in FIG. 9, the re-phosphorylation was determined to have a yield of about 99%.

Figure 10:
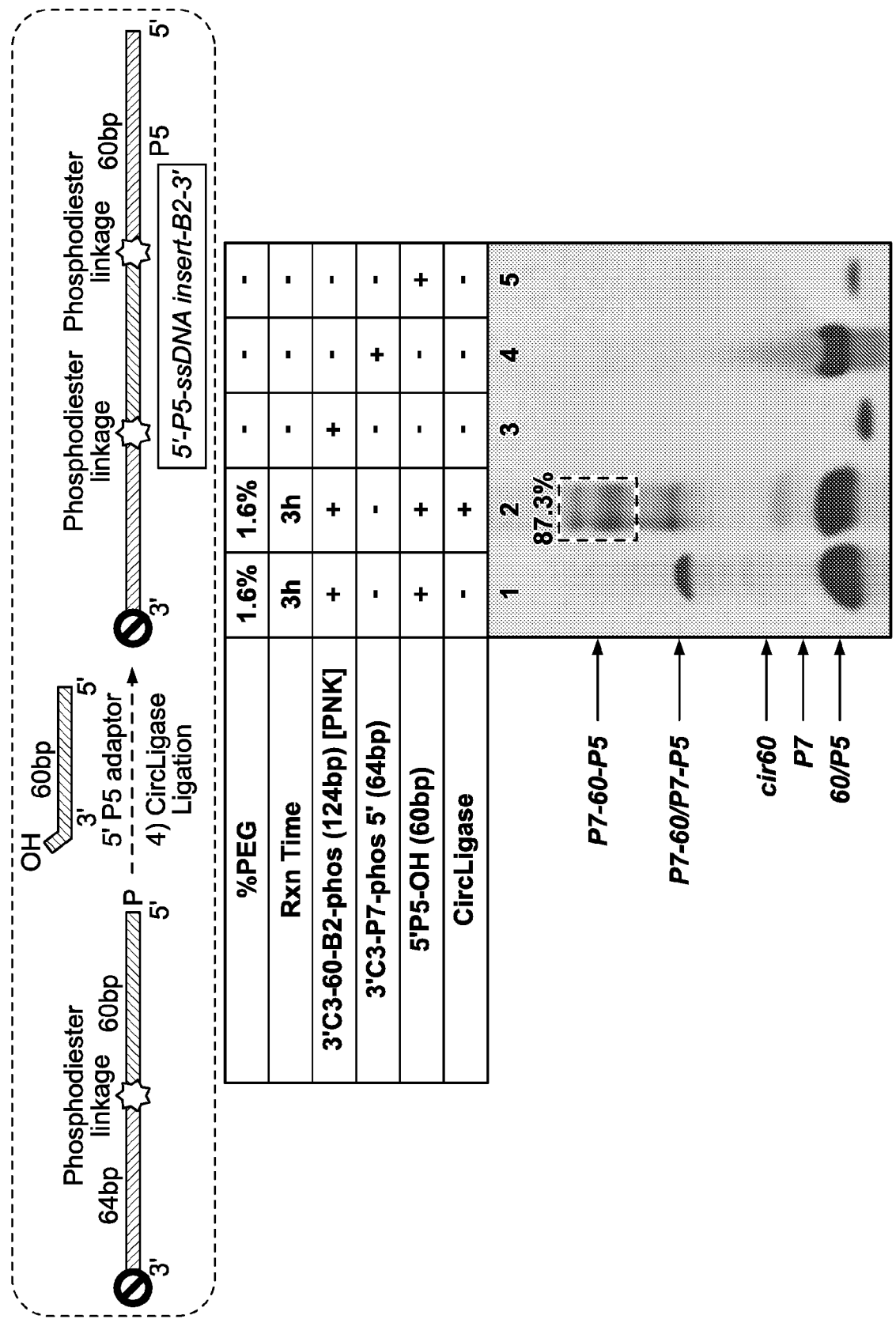
FIG. 10 depicts the results of an experiment to ligate a 60-mer P5 adaptor having a non-phosphorylated 5' end (5'P5-OH) to the 5' end of a 124-mer single-stranded nucleic acid (3'C3-60-B2-Phos). The 124-mer single-stranded nucleic acid includes a ligated 64-mer adaptor with a 3' blocking group (3'C3-P7-phos 5'). The top panel is a schematic showing the ligation. The table outlines conditions for reactions performed and run on the gel shown in the lower panel including TS2126 RNA ligase (CIRCLIGASE™).

To examine the second ligation step, a 60-mer P5 adaptor having a non-phosphorylated 5' end (5'P5-OH) was ligated to the 5' end of a 124-mer single-stranded nucleic acid (3'C3-60-B2-Phos) using TS2126 RNA ligase (CIRCLIGASE™) in a reaction volume containing 1.6% PEG. The 124-mer single-stranded nucleic acid included a ligated 64-mer adaptor with a 3' blocking group (3'C3-P7-phos 5'). As shown in FIG. 10, the yield for this ligation step (Lane 2) was determined to be >85%. Thus, the overall yield of the 4-step ssDNA library preparation approach was >80%.

Example 2—Ligation of Adaptors to Cell-Free Target Nucleic Acids

Figure 11:
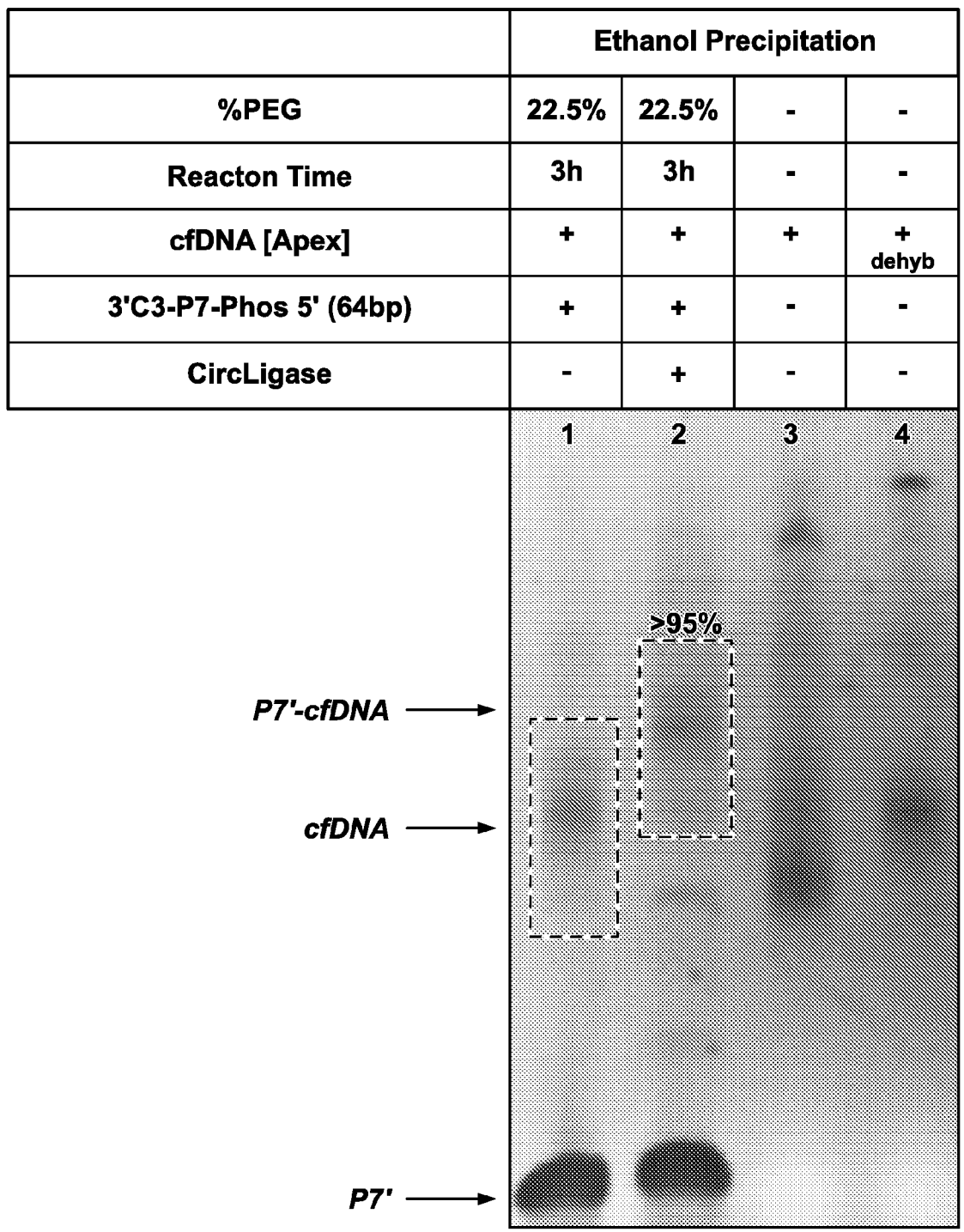
FIG. 11 depicts the results of an experiment to ligate a 64-mer P7' adaptor containing a 3' blocking group (3'C3-P7-phos 5') to the 3' end of single-stranded dephosphorylated cell-free DNA (cfDNA). The table outlines conditions for reactions performed and run on the gel shown in the lower panel including TS2126 RNA ligase (CIRCLIGASE™).

The scheme outlined in FIG. 1 was performed using cell-free DNA (cfDNA). Double-stranded target nucleic acids were dephosphorylated using a heat-labile alkaline phosphatase (APEX™ phosphatase), and dehybridized to form single-stranded target nucleic acids. To examine the initial ligation step, a 64-mer P7' adaptor containing a 3' blocking group (3'C3-P7-phos 5') was ligated to the 3' end of single-stranded dephosphorylated cell-free DNA (cfDNA) using TS2126 RNA ligase (CIRCLIGASE™) in a reaction volume containing 22.5% PEG for 3 hours. As shown in FIG. 11, the yield for this ligation step (Lane 2) was determined to be greater than 95%.

Figure 12:
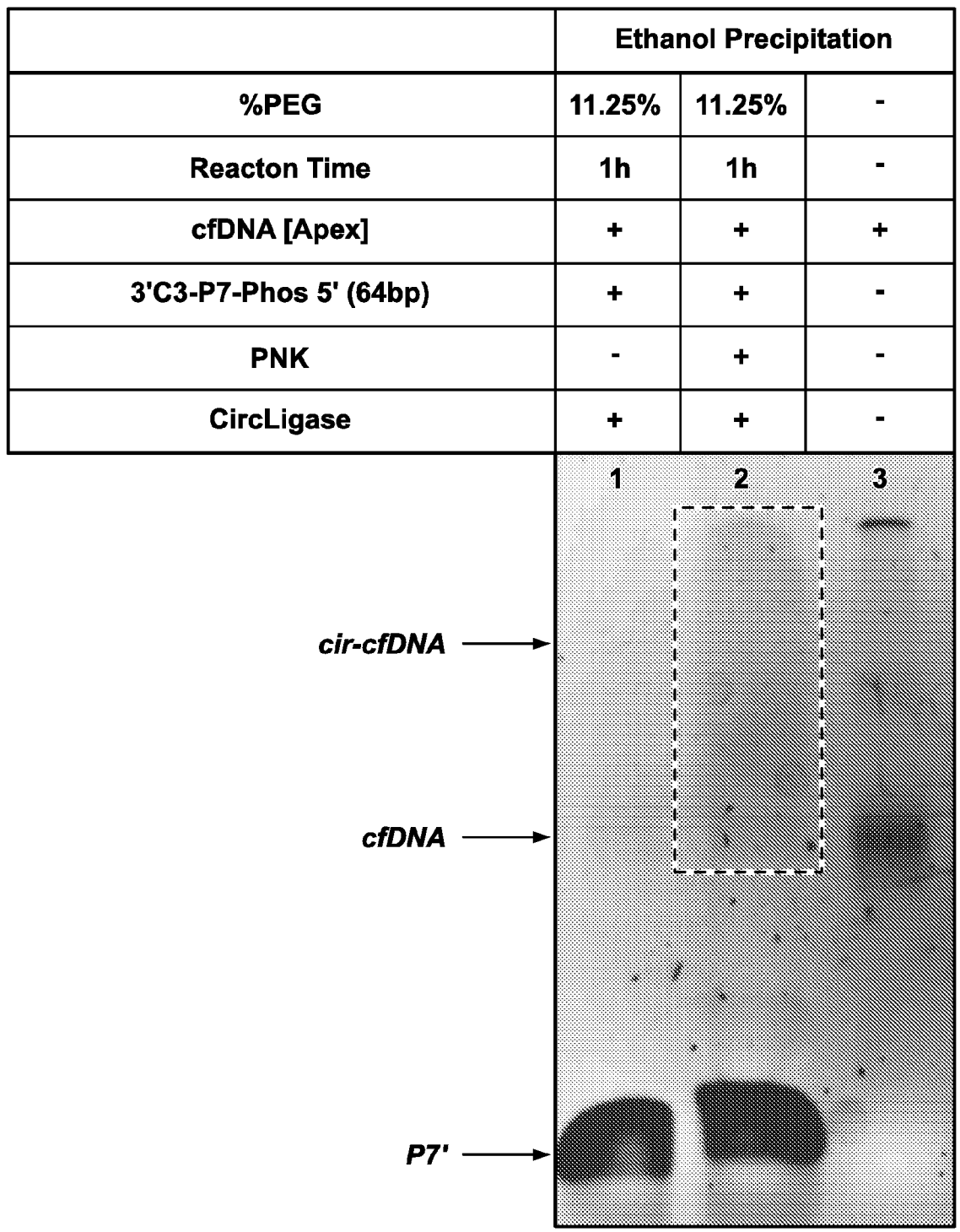
FIG. 12 depicts the results of an experiment in which dephosphorylated cfDNA (cfDNA [Apex]) was treated with a kinase (PNK), and a 64-mer P7' adaptor containing a 3' blocking group (3'C3-P7-phos 5') was ligated to the 3' end of the re-phosphorylated cfDNA. The table outlines conditions for reactions performed and run on the gel shown in the lower panel including TS2126 RNA ligase (CIRCLIGASE™).

To examine the kinase step, dephosphorylated cfDNA (cfDNA [Apex]) was treated with T4 polynucleotide kinase (PNK), and a 64-mer P7' adaptor containing a 3' blocking group (3'C3-P7-phos 5') was ligated to the 3' end of the re-phosphorylated cfDNA. The reaction was performed in a volume containing 11.25% PEG for 1 hour (FIG. 12).

Figure 13:
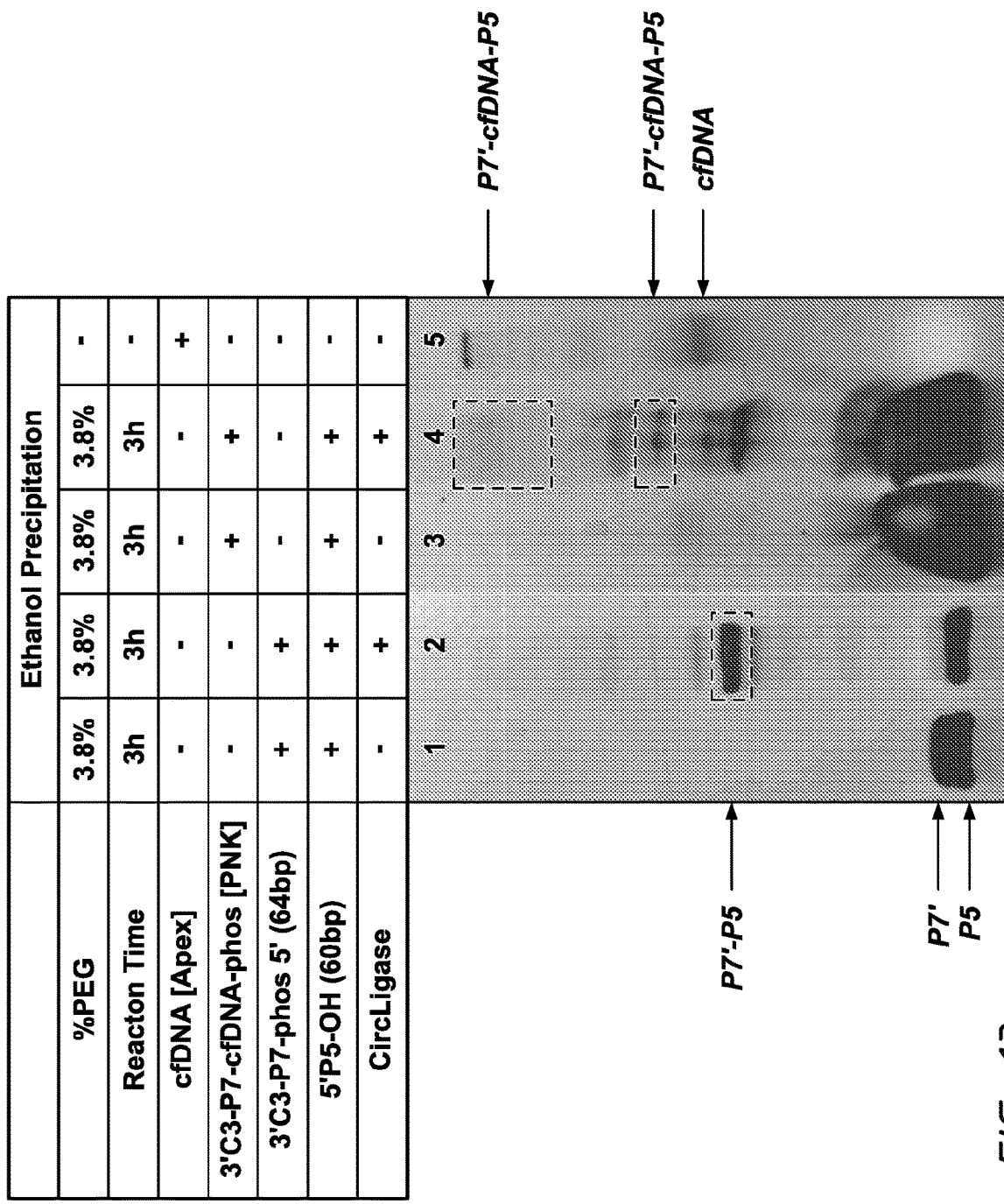
FIG. 13 depicts the results of an experiment in which a 64-mer P7' adaptor containing a 3' blocking group (3'C3-P7-phos 5') was ligated to the 3' end of dephosphorylated cfDNA, the resulting first ligated product (3'C3-P7-cfDNA-phos 5') was treated with a kinase (PNK), and a 60-mer P5 adaptor having a non-phosphorylated 5' end (5'P5-OH) was ligated to the 5' end of the first ligation product to form a second ligation product (P7'-cfDNA-P5). The table outlines conditions for reactions performed and run on the gel shown in the lower panel including TS2126 RNA ligase (CIRCLIGASE™).

To examine the second ligation step, a 64-mer P7' adaptor containing a 3' blocking group (3'C3-P7-phos 5') was ligated to the 3' end of dephosphorylated cfDNA, the resulting first ligated product (3'C3-P7-cfDNA-phos 5') was treated with a kinase (PNK), and a 60-mer P5 adaptor having a non-phosphorylated 5' end (5'P5-OH) was ligated to the 5' end of the first ligation product to form a second ligation product (P7'-cfDNA-P5). The reaction was performed using TS2126 RNA ligase (CIRCLIGASE™) in a reaction volume containing 3.8% PEG. FIG. 13 shows ligation products (P7'-cfDNA-P5) and (P7'-P5).

Example 3—Analysis of Ligation Products

Ligation products from Example 2 were resolved on a gel, bands of ligation products were extracted from the gel, extracted ligation products were amplified, and amplified products were resolved using capillary electrophoresis (Bio-Analyzer, Agilent).

Figure 14:
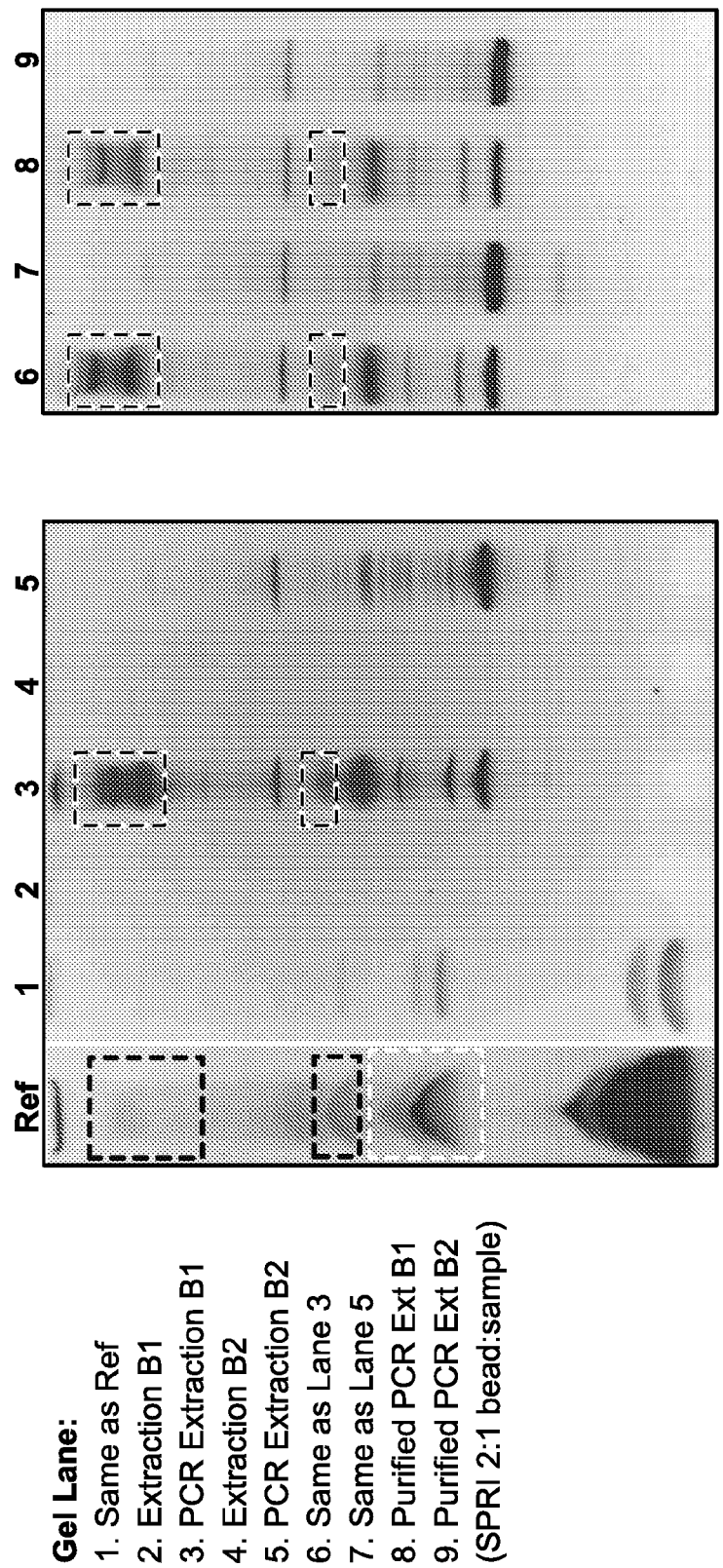
FIG. 14 depicts gels showing ligation products of Example 2, and amplification products from ligation products Extract B1 and Extract B2. In the 'Ref' lane, Extract B1 is marked by two black boxes, and Extract B2 is marked by a single white box.

Ligation products were resolved on a gel, and bands Extract B1 and Extract B2 were excised from the gel. As shown in FIG. 14, in lane 'REF' Extract B1 is marked by two black boxes, and Extract B2 is marked by a single white box. Extracts were amplified by PCR that included non-PCR (non-amplifiable) P7 primers in a ratio with PCR P7 primers from 1:40 to 1:20, for 24 cycles. PCR products were extracted using solid phase reversible immobilization (SPRI) beads at a ratio with sample of 2:1. Results are shown in FIG. 14.

Figure 15:
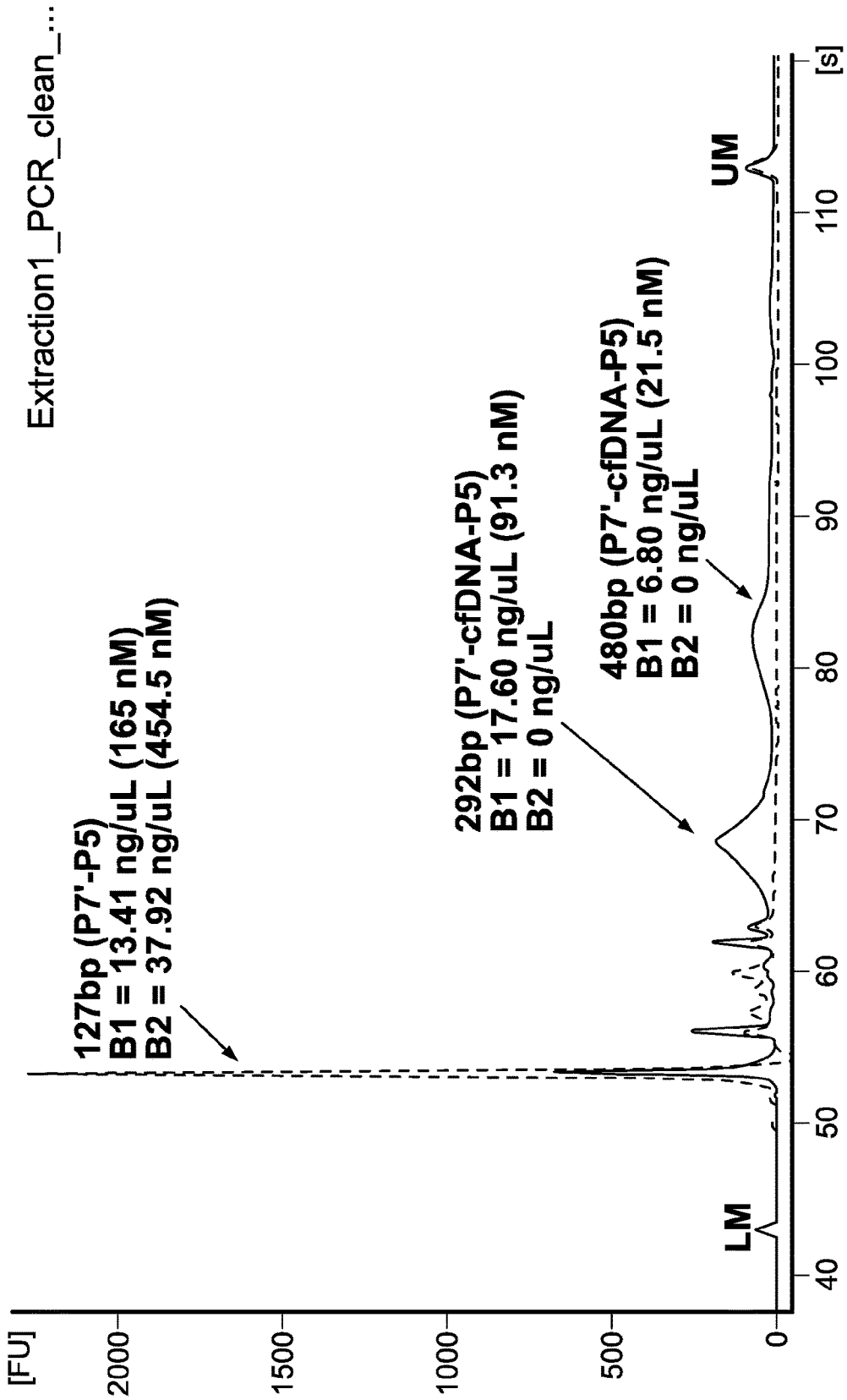
FIG. 15 depicts an electropherogram of amplified ligation products, Extract B1 and Extract B2. Peaks denote a 126 bp primer-dimer (P7'-P5), a 292 bp (P7'-cfDNA-P5) and a 480 bp (P7'-cfDNA-P5) species.

Amplified products of Extracts B1 and B2 were further analyzed by capillary electrophoresis (BioAnalyser, Agilent). As shown in FIG. 15, Extract B2 contained predominantly a 127 bp (P7'-P5) species, and Extract B1 included a 292 bp (P7'-cfDNA-P5) species, and a 480 bp (P7'-cfDNA-P5) species.

Figure 16:
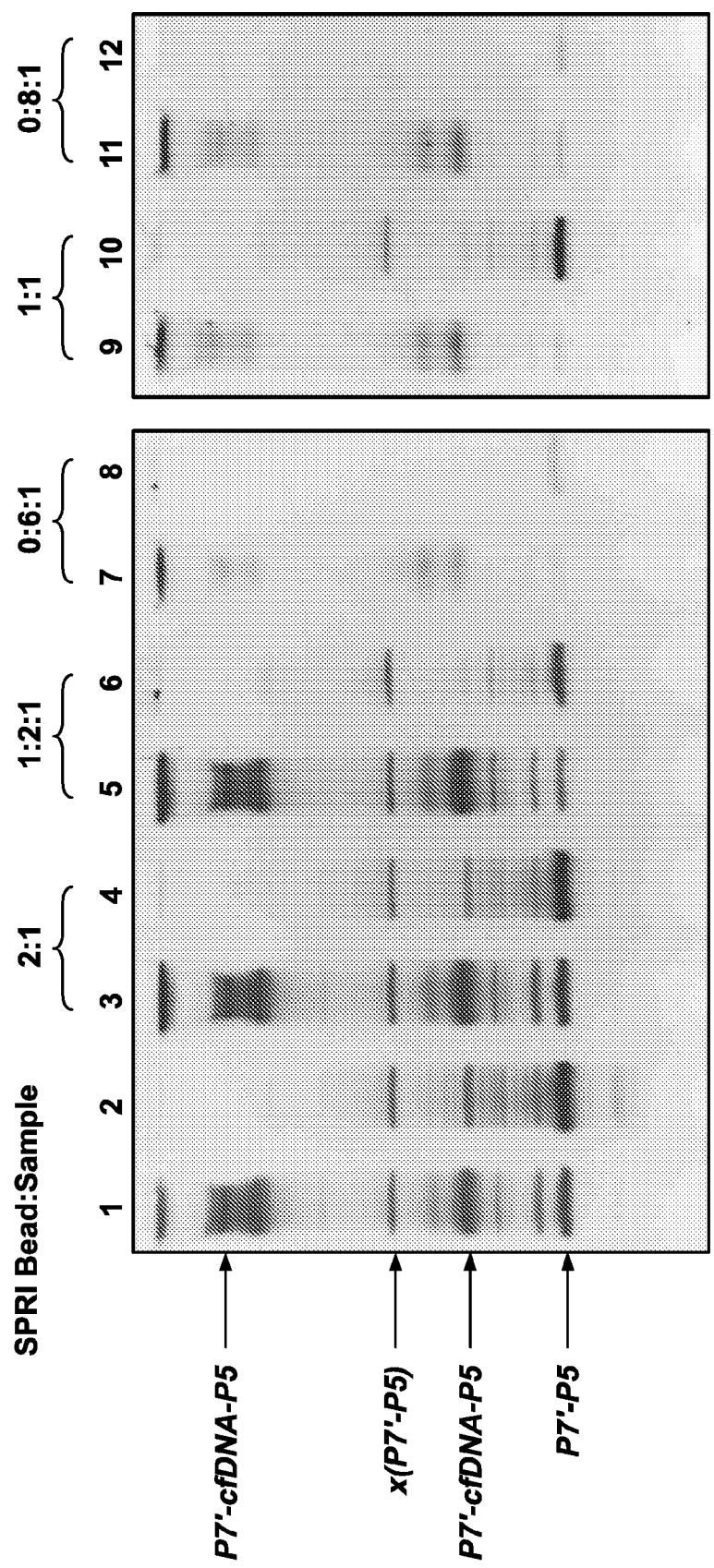
FIG. 16 depicts gels that show the results of using solid phase reversible immobilization (SPRI) beads at various ratios to extract amplification products.

The amount of SPRI beads used to purify gel extracts was varied to determine a ratio effective to remove primer-dimers (FIG. 16). An SPRI bead:sample (v:v) of 1.2:1 was most effective in removing primer-dimers without the loss of a significant portion of the cfDNA library.

Example 4—Capturing Non-Ligated P7' Primers

Excess non-ligated P7' primers were removed using a scheme outlined in FIG. 5. Briefly, a P7 primer complementary to the P7' adaptor primer was added to the reaction volume after ligation of the P7' adaptor primer to the 3' end of the target nucleic. The P7 primer included blocking groups at its 5' and 3' ends. After addition of the P7 primer, the P5 adaptor was ligated to the 5' end of the re-phosphorylated ligated target nucleic acid.

Figure 17:
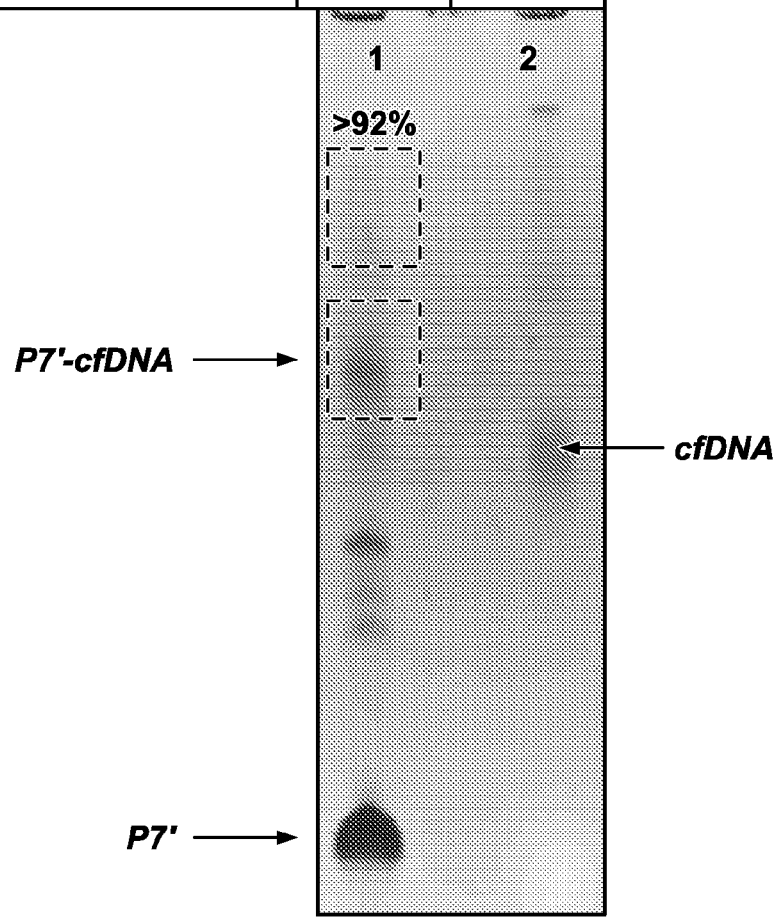
FIG. 17 depicts the results of an experiment to ligate a 63-mer P7' adaptor containing a 3' blocking group (3'C3-P7'-Phos 5') to the 3' end of single-stranded dephosphorylated cfDNA. The table outlines conditions for reactions performed and run on the gel shown in the lower panel including TS2126 RNA ligase (CIRCLIGASE™).
Figure 18:
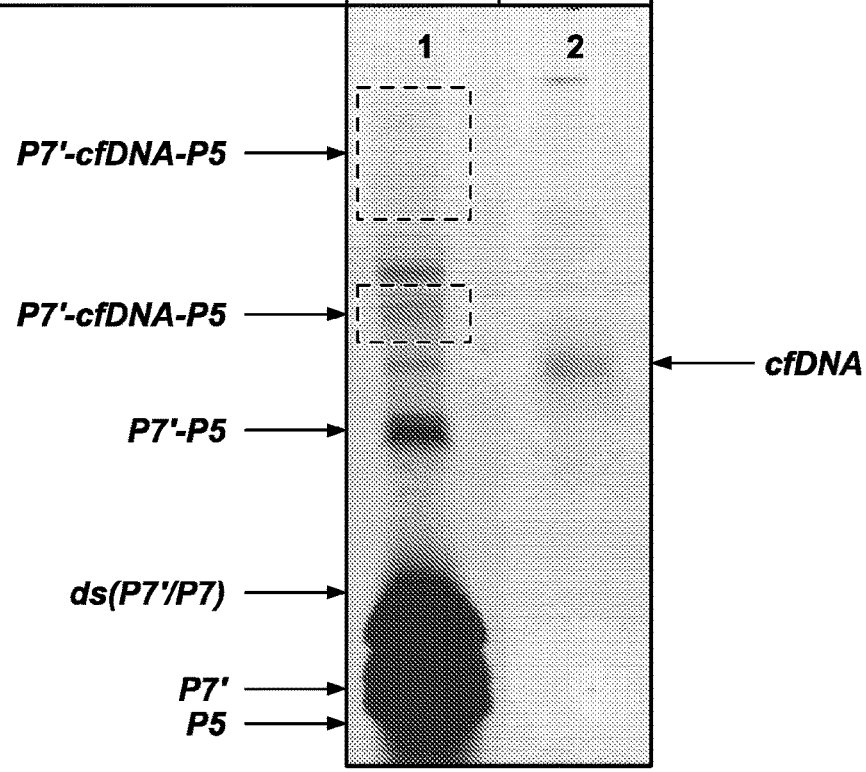
FIG. 18 depicts the results of an experiment to ligate a 60-mer P5 adaptor having a non-phosphorylated 5' end (5'P5-OH) to the 5' end of a first ligation product (3'C3-P7'-cfDNA-phos5') in the presence of a 63-mer P7 capture probe (3'C3-P7-C35') which contains 5' and 3' blocking groups. The table outlines conditions for reactions performed and run on the gel shown in the lower panel including TS2126 RNA ligase (CIRCLIGASE™).

A 63-mer P7' primer (3'C3-P7'-phos5') was ligated to the 3' ends of cfDNA in a reaction volume containing 25% PEG. As shown in FIG. 17, the yield of ligated product was >95%. To examine ligation in the presence of a capture probe, a 60-mer P5 adaptor having a non-phosphorylated 5' end (5'P5-OH) was ligated to the 5' end of a first ligation product (3'C3-P7'-cfDNA-phos5') in the presence of a 63-mer P7 capture probe (3'C3-P7-C35') which contained 5' and 3' blocking groups. The reaction was performed in a reaction volume containing 6.5% PEG. FIG. 18 shows ligation products (P7'-cfDNA-P5) and (P7'-P5).

Figure 19:
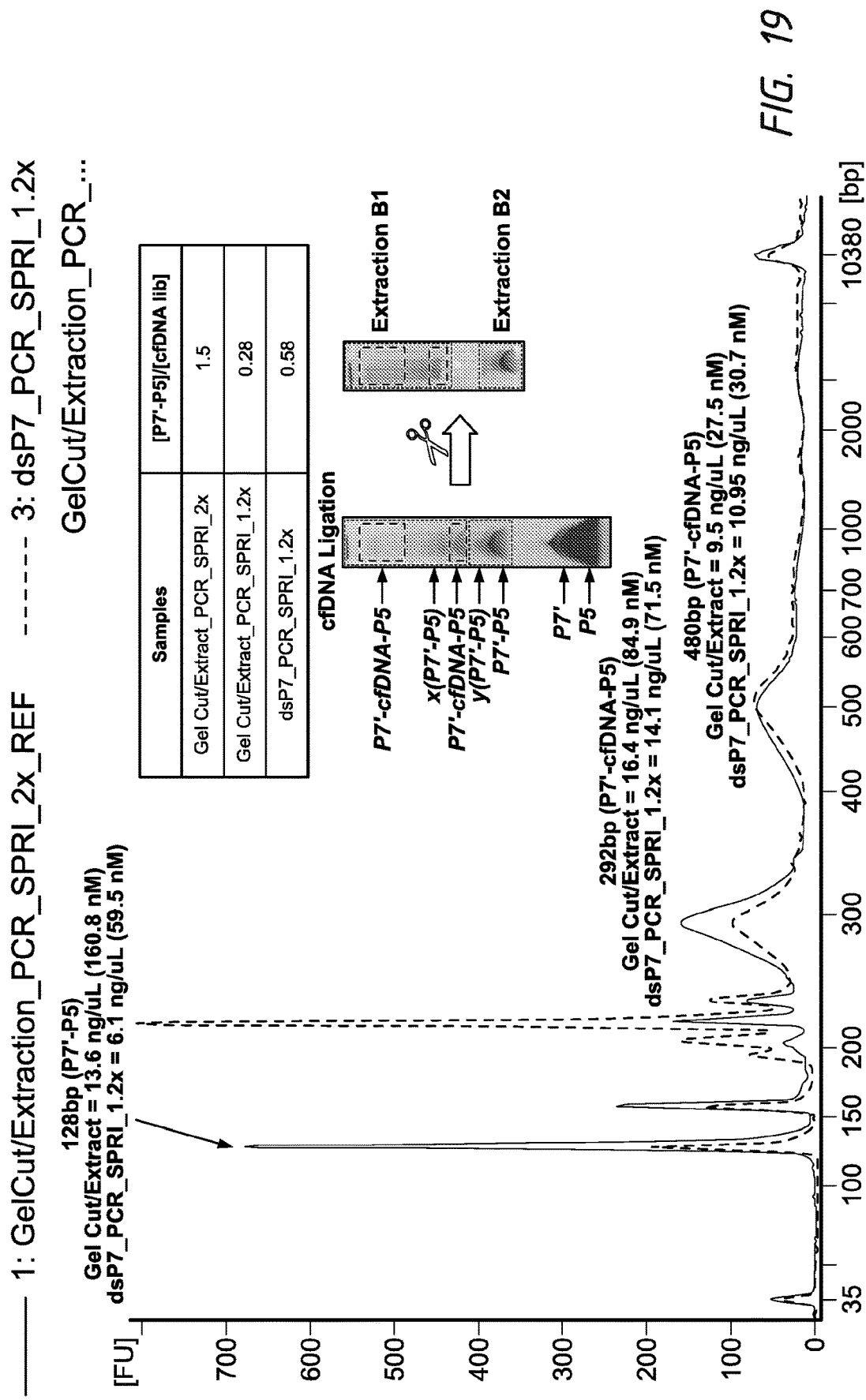
FIG. 19 depicts an electropherogram analysis of amplified ligation products, Extract B1 and Extract B2. Peaks denote a 126 bp primer-dimer (P7'-P5), a 292 bp (P7'-cfDNA-P5) and a 480 bp (P7'-cfDNA-P5) species.
Figure 20:
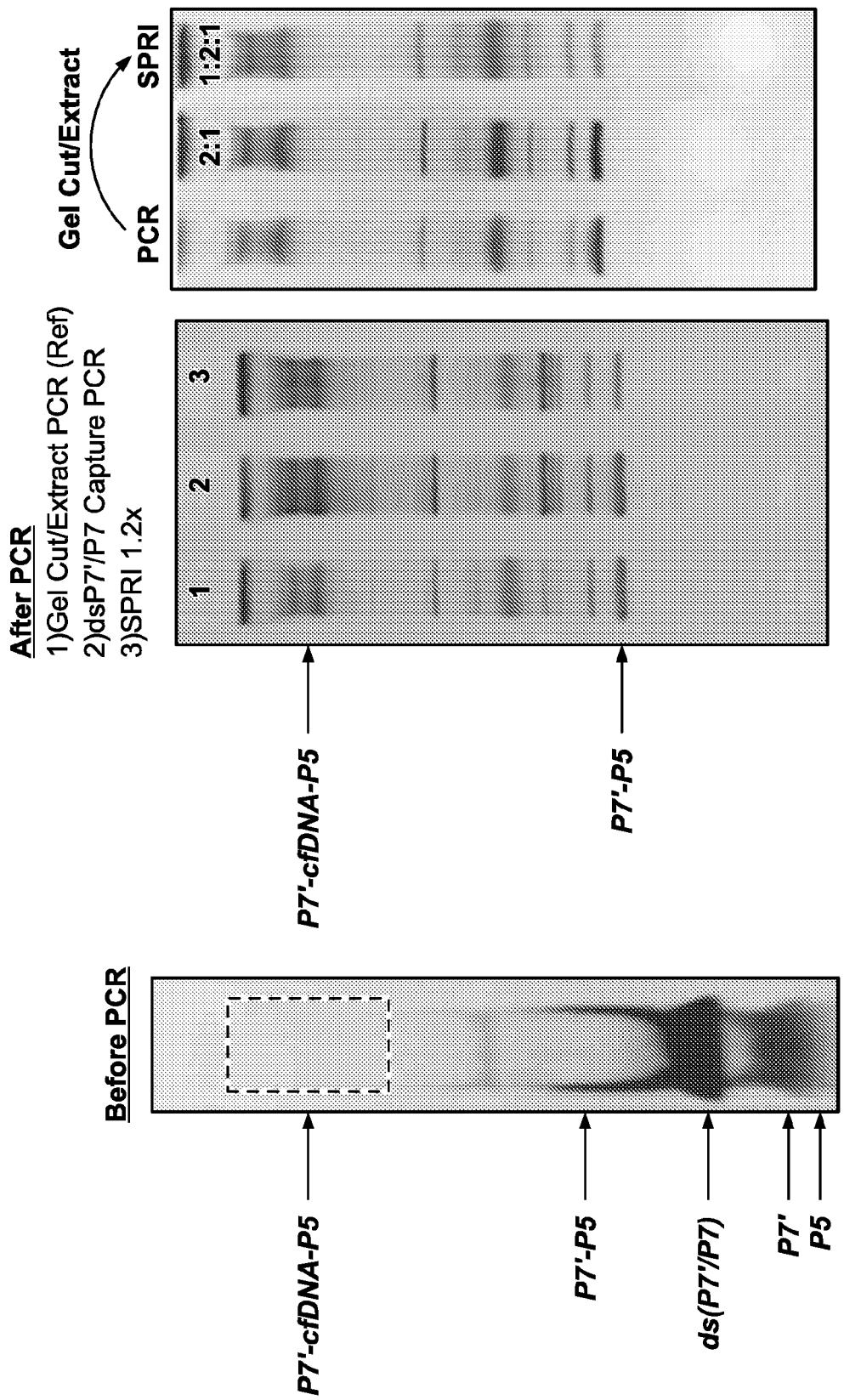
FIG. 20 depicts gels of ligation products before amplification, after amplification, and after extraction with SPRI beads.

Ligation products were analyzed further. As shown in FIG. 19, ligation products were resolved by size on a gel, certain bands were extracted from the gel, and Extract B1 and Extract B2 were amplified. Amplified products were analyzed by capillary electrophoresis and included a 127 bp (P7'-P5) species, a 292 bp (P7'-cfDNA-P5) species, and a 480 bp (P7'-cfDNA-P5) species. FIG. 20 depicts gels of ligation products before amplification, after amplification, and after extraction with SPRI beads.

Incorporation of non-PCR P7 to capture excess P7' significantly reduced the formation of primer-dimers. In addition, primer-dimers were significantly reduced by removal using 1.2×SPRI without a significant loss of the cfDNA library.

Example 5—Ligation of Single-Strand Nucleic Acids Conjugated to Beads

Figure 21:
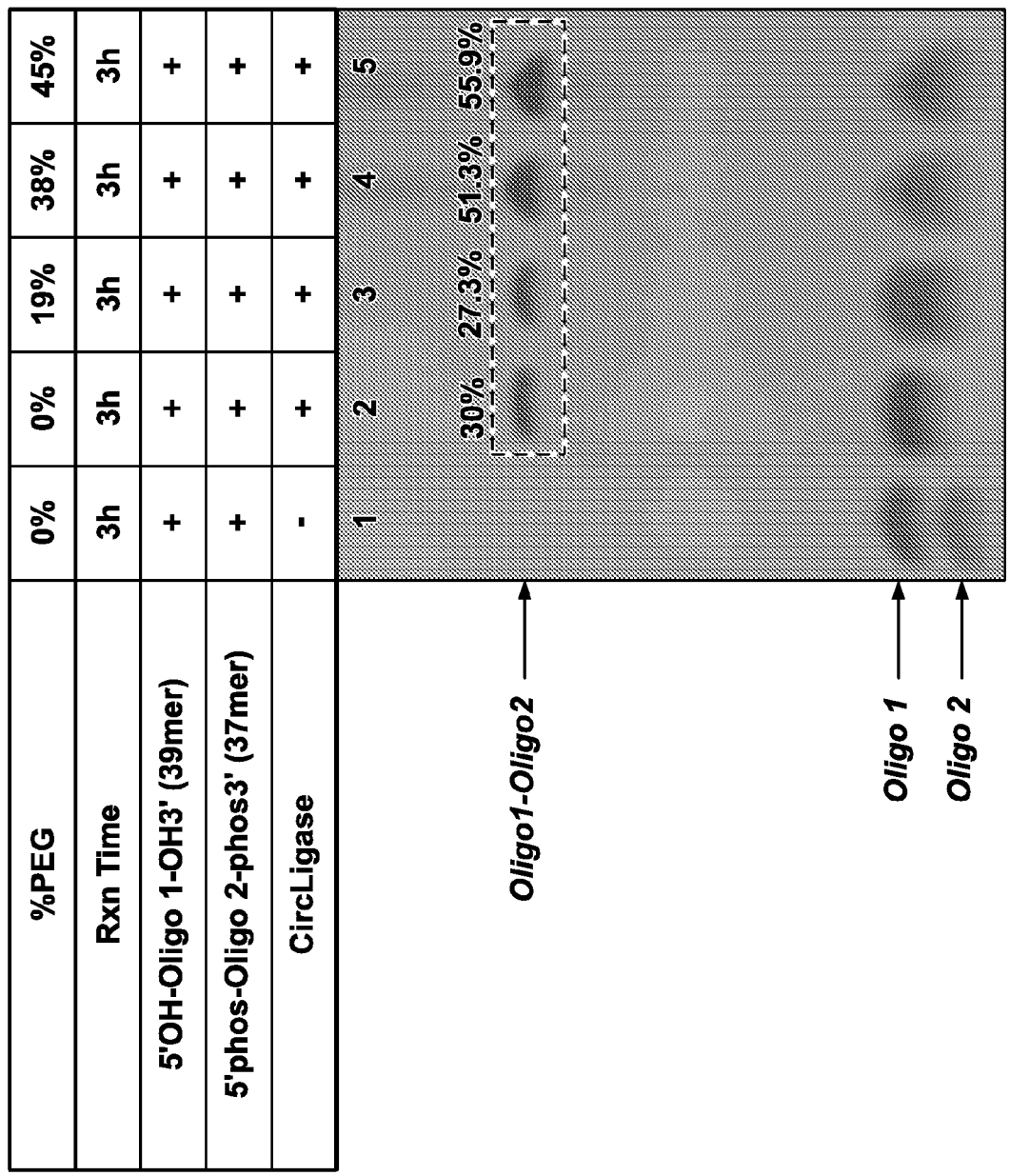
FIG. 21 depicts the results of an experiment to ligate a 39-mer Oligo 1 having a dephosphorylated 5' end (5'OH-Oligo 1-OH3') to a 37-mer Oligo 2 having a phosphorylated 3' blocking group (5'phos-Oligo 2-phos3') in the presence of various concentration of polyethylene glycol (PEG). The table outlines conditions for reactions performed and run on the gel shown in the lower panel including TS2126 RNA ligase (CIRCLIGASE™).

The efficiency of ligation between two oligomers (oligo 1 and oligo 2) in various concentration of PEG was examined. Oligo 1 included a blocked 3' end (OH), and oligo 2 included a blocked 5' end (phos), thus ligation yielded a single ligated oligo1-oligo2 product. Reaction conditions included: 10 µmol of each oligo+2 µL of 10× buffer+1 µL of 1 mM ATP, 1 µL of 50 mM $MnCl_2$, 1 µL of TS2126 RNA ligase CIRCLIGASE (100 U/µL)+15 µL of 0, 25, 50, or 60% PEG in a final reaction volume of 20 µL, with 0, 19, 38, and 45% PEG, respectively. Results are shown in FIG. 21. A reaction volume containing 45% PEG provided a yield of ligated oligo 1 and oligo 2 of 55.9%.

Figure 22:
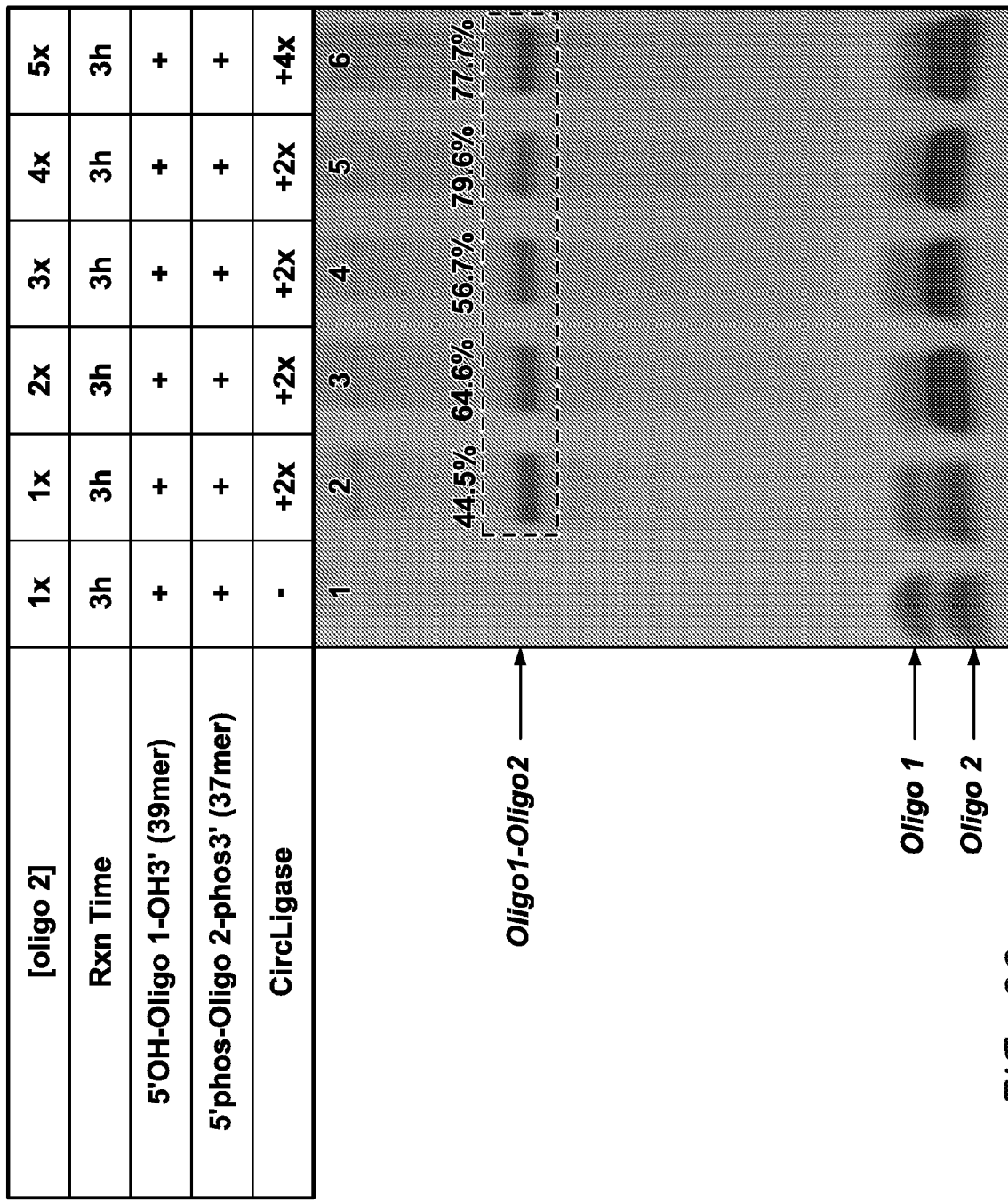
FIG. 22 depicts the results of an experiment to ligate a 39 bp Oligo 1 having a dephosphorylated 5' end (5'OH-Oligo 1-OH3') to a 37 bp Oligo 2 having a phosphorylated 3' blocking group (5'phos-Oligo 2-phos3') with various ratios of Oligo1:Oligo 2. The table outlines conditions for reactions performed and run on the gel shown in the lower panel including TS2126 RNA ligase (CIRCLIGASE™).

The efficiency of ligation between oligo 1 and oligo 2 with various concentration of oligo 2 was examined. Reaction conditions included: 10 µmol of oligo 1+10× pmol of oligo 2+2 µL of 10× buffer+1 µL of 1 mM ATP, 1 µL of 50 mM $MnCl_2$, 2 of TS2126 RNA ligase (CIRCLIGASE™) (100 U/µL)+15 µL of 60% PEG provided a final reaction volume of 20 µL with 45% PEG. Results are shown in FIG. 22. A reaction volume containing a 4× excess of oligo 2, and +2×TS2126 RNA ligase (CIRCLIGASE™) provided a yield of ligated oligo 1 and oligo 2 of 79.6%.

Figure 23:
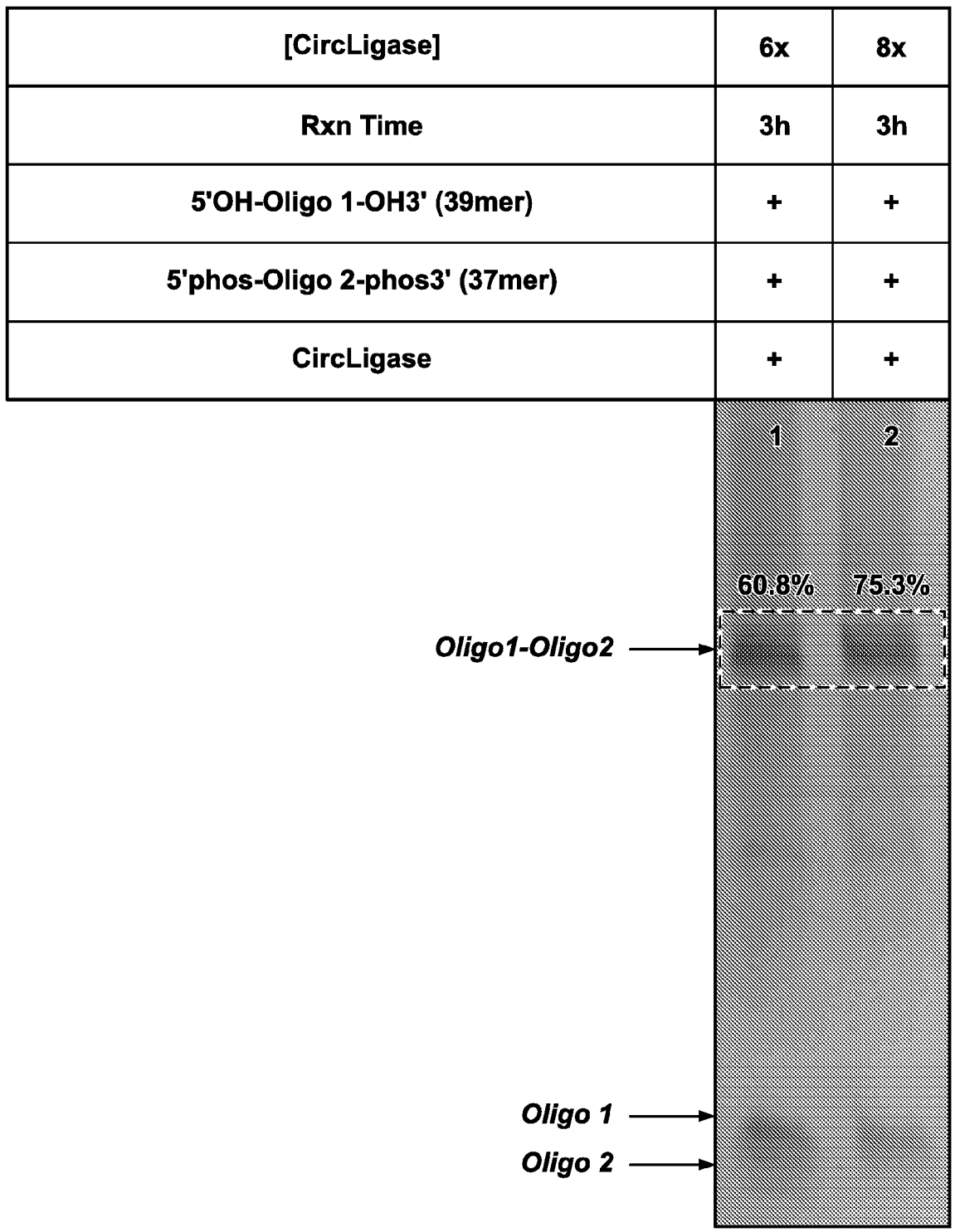
FIG. 23 depicts the results of an experiment to ligate a 39 bp Oligo 1 having a dephosphorylated 5' end (5'OH-Oligo 1-OH3') to a 37 bp Oligo 2 having a phosphorylated 3' blocking group (5'phos-Oligo 2-phos3') with various amounts of TS2126 RNA ligase (CIRCLIGASE™). The table outlines conditions for reactions performed and run on the gel shown in the lower panel.

The efficiency of ligation between oligo 1 and oligo 2 with various concentrations of TS2126 RNA ligase (CIRCLIGASE™) was examined. Reaction conditions included: 10 µmol of each oligo+2 µL of 10× buffer+1 µL of 1 mM ATP, 1 µL of 50 mM $MnCl_2$, X µL of TS2126 RNA ligase (CIRCLIGASE™) (100 U/µL)+15 µL of 60% PEG provided a final reaction volume of 20 µL with 45% PEG. Results are shown in FIG. 23. A reaction volume containing an 8× concentration of TS2126 RNA ligase (CIRCLIGASE™) provided a yield of ligated oligo 1 and oligo 2 of 75.3%.

Oligo 1 was conjugated to beads via hydrazine-aldehyde coupling. 39-mer oligo 1 included two uracil bases which could be cleaved using uracil DNA glycosylase (UDG) to produce a shorter 27-mer oligo (oligo 1*).

Figure 24:
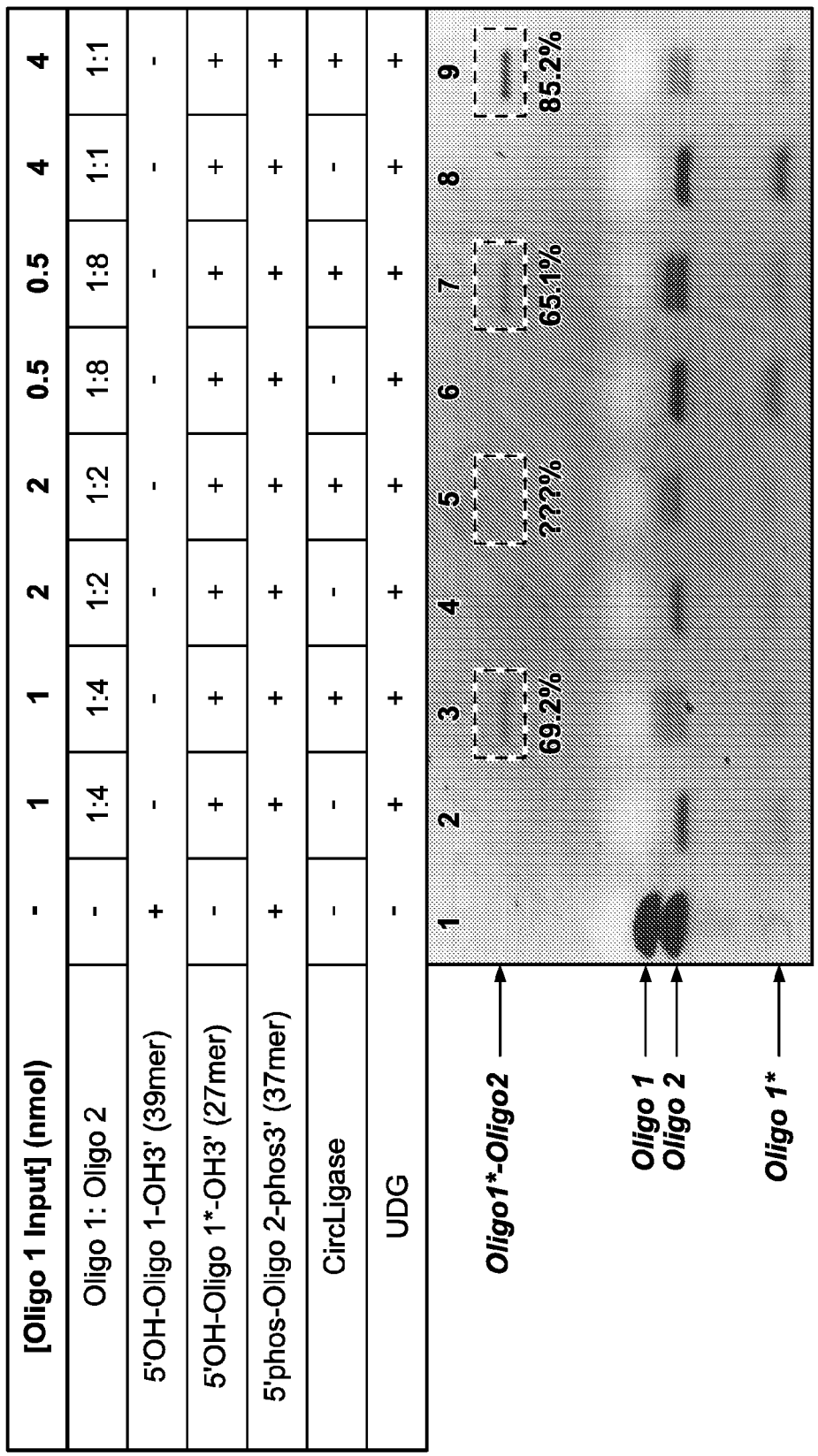
FIG. 24 depicts the results of an experiment to ligate a 37-mer Oligo 2 having a phosphorylated 3' blocking group (5'phos-Oligo 2-phos3') to a 39-mer Oligo 1 having a dephosphorylated 5' end (5'OH-Oligo 1-OH3') which was conjugated to beads. Ligation products were assayed by cleavage from beads using uracil-DNA glycosylase (UDG) which cut an uracil site in Oligo 1. The table outlines conditions for reactions performed and run on the gel shown in the lower panel including TS2126 RNA ligase (CIRCLIGASE™).
Figure 25:
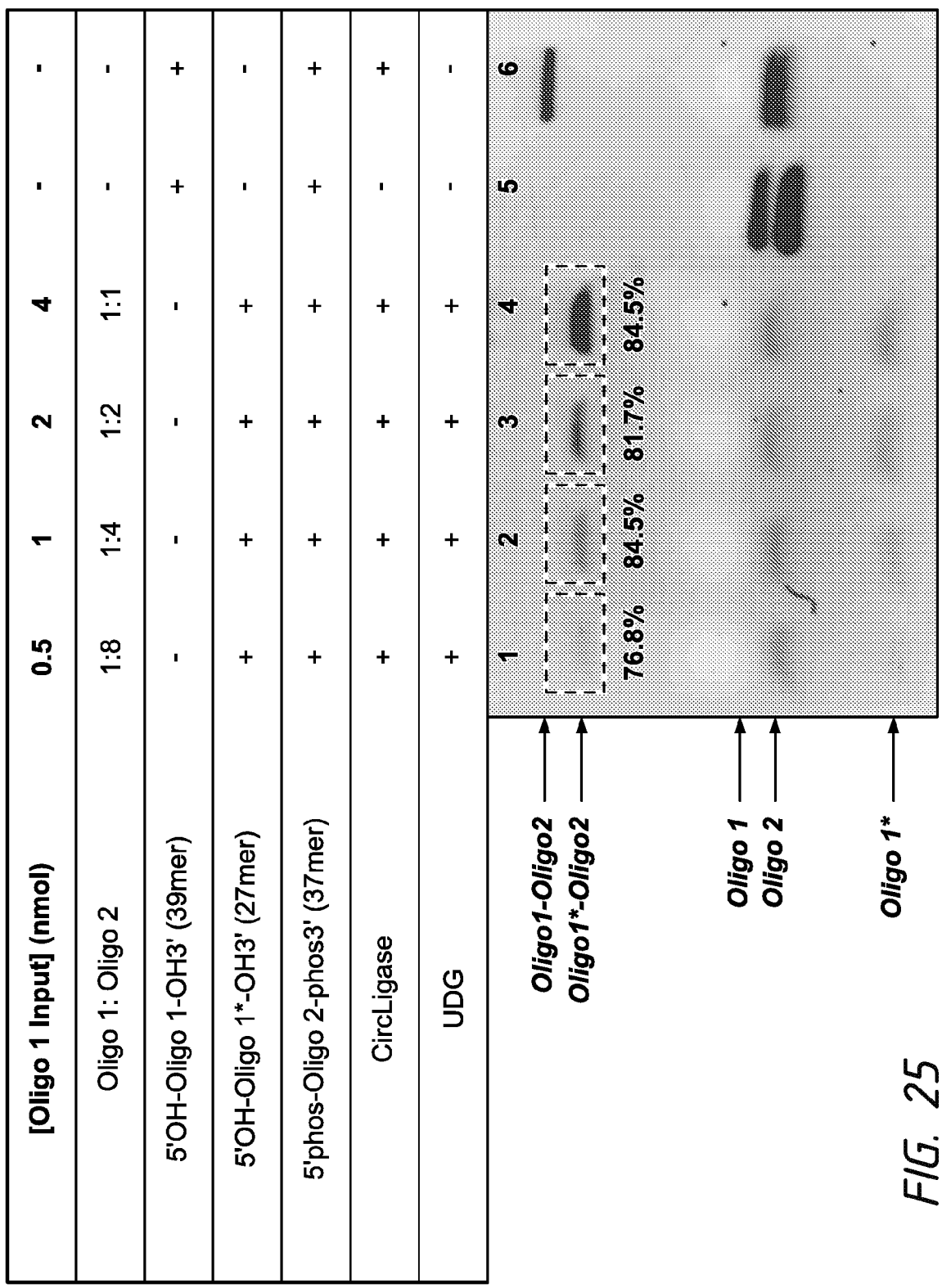
FIG. 25 depicts the results of an experiment to ligate a 37-mer Oligo 2 having a phosphorylated 3' blocking group (5'phos-Oligo 2-phos3') to a 39-mer Oligo 1 having a dephosphorylated 5' end (5'OH-Oligo 1-OH3') which was conjugated to beads, in a final reaction volume having 45% PEG. The table outlines conditions for reactions performed and run on the gel shown in the lower panel including TS2126 RNA ligase (CIRCLIGASE™).

Various concentrations of oligo 1 conjugated to beads was examined in ligation reaction. Ligation of oligo 2 to conjugated oligo 1 was assayed by subsequent treatment with UDG. Ligation reaction conditions assumed that the amount of oligo 1 used for bead attachment was equal to the amount of oligo 1 on beads. Four concentrations of total oligo 1 input were tested: 0.5 nmol, 1 nmol, 2 nmol, and 4 nmol. 10% of total bead solution was used, thus the oligo 1 amount in each reaction was assumed to be equal to 0.1 nmol, 0.2 nmol, 0.3 nmol and 0.4 nmol. Reaction mixture: 10 µL of bead solution (2× concentrated), oligo 2 (0.4 nmol), 2 µL of 10× buffer, 1 µL of 1 mM ATP, 1 µL of 50 mM $MnCl_2$, 1 µL of TS2126 RNA ligase (CIRCLIGASE™) (100 U/µL)+5 µL of 90% PEG to provide a final reaction volume of 20 µL with 22.5% PEG. Reactions were incubated at 60° C. for 3 h, and inactivated at 80° C. for 10 min. Oligo 1:Oligo 2 ratios in the reactions: 0.05 nmol (1:8); 0.1 nmol (1:4), 0.2 nmol (1:2), 0.4 nmol (1:1). Uracil cleaving was performed with 10 µL of LMX1 in a final reaction volume 10 µL, and incubating at 37° C. for 1 hour. Results are shown in FIG. 24. A reaction volume containing a 1:1 ratio of oligo 1:oligo 2, provided a yield of ligated oligo 1 and oligo 2 of 85.2%. The assay was repeated for final reaction volumes having 45% PEG. Results are shown in FIG. 25. A reaction volume containing a 1:1 ratio of oligo 1:oligo 2, provided a yield of ligated oligo 1 and oligo 2 of 84.5%.

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method of preparing a nucleic acid library, comprising:
   - (a) obtaining a plurality of nucleic acids, wherein the plurality of nucleic acids is single-stranded nucleic acids;
   - (b) dephosphorylating the 5' ends of the single-stranded nucleic acids;
   - (c) contacting a single-stranded first adaptor with the single-stranded nucleic acids in the presence of a ligase, wherein the 3' end of the single-stranded first adaptor comprises a blocking group, thereby obtaining ligated single-stranded nucleic acids and non-ligated single-stranded first adaptors;
   - (d) hybridizing the non-ligated single-stranded first adaptors with a capture probe;
   - (e) phosphorylating the 5' ends of the ligated single-stranded nucleic acids; and
   - (f) ligating a second adaptor to the 5' ends of the phosphorylated ligated single-stranded nucleic acids in the presence of the ligase, thereby obtaining a library of nucleic acids.

2. The method of claim 1, wherein the second adaptor is attached to a substrate.

3. The method of claim 1, wherein the 3' end of the capture probe comprises a blocking group.

4. The method of claim 1, wherein the 5' end of the capture probe comprises a blocking group.

5. The method of claim 1, wherein steps (b)-(f) are performed in a single reaction volume.

6. The method of claim 1, wherein the blocking group comprises a 3'-spacer C3 or a dideoxynucleotide.

7. The method of claim 1, wherein the ligation of the single-stranded first adaptor and/or the ligating of the second adaptor is performed in the presence of a volume excluding agent selected from the group consisting of a polyethylene glycol (PEG), dextran, hetastarch, Ficoll, and polyvinylpyrrolidone.

8. The method of claim 7, wherein, the first ligation step and/or second ligation step is performed in a reaction volume comprising at least about 37% (wt/vol) PEG.

9. The method of claim 1, wherein the capture probe is in solution.

10. The method of claim 1, wherein the single-stranded first adaptor and/or second adaptor comprises a sequencing primer binding site or an adaptor index.

11. The method of claim 10, wherein the sequencing primer binding site comprises a P7 sequence, a P5 sequence, or a complement of a P7 sequence, a complement of a P5 sequence, a reverse complement of a P7 sequence, or a reverse complement of a P5 sequence.

12. The method of claim 10, wherein the single-stranded first adaptor comprises a first adaptor index and the second adaptor comprises a second adaptor index.

13. The method of claim 12, wherein the first adaptor index is different from the second adaptor index.

14. The method of claim 1, wherein the average size of a nucleic acid of the plurality of nucleic acids is less than about 200 nucleotides.

15. The method of claim 1, wherein step (f) is performed subsequent to step (d).

16. The method of claim 1, wherein step (f) is performed in a reaction mixture comprising the capture probe.

17. The method of claim 1, wherein steps (b)-(f) are performed sequentially in a single reaction mixture.

* * * * *

UNITED STATES PATENT AND TRADEMARK OFFICE
CERTIFICATE OF CORRECTION

| | | |
|---|---|---|
| PATENT NO. | : 11,518,993 B2 | |
| APPLICATION NO. | : 16/494902 | |
| DATED | : December 6, 2022 | |
| INVENTOR(S) | : Chen et al. | |

It is certified that error appears in the above-identified patent and that said Letters Patent is hereby corrected as shown below:

In the Drawings

Sheet 9 of 27 (FIG. 8), Line 8 (approx.), delete "3'OH-60-0H 5'" and insert -- 3'OH-60-OH 5' --.

Sheet 10 of 27 (FIG. 9), Line 8 (approx.), delete "3'OH-60-0H 5'" and insert -- 3'OH-60-OH 5' --.

Sheet 12 of 27 (FIG. 11), Line 3, delete "Reacton" and insert -- Reaction --.

Sheet 13 of 27 (FIG. 12), Line 3, delete "Reacton" and insert -- Reaction --.

Sheet 14 of 27 (FIG. 13), Line 3, delete "Reacton" and insert -- Reaction --.

In the Specification

Column 2, Line 17, delete "phophate" and insert -- phosphate --.

Column 7, Line 13, delete "kinase (PNK)," and insert -- polynucleotide kinase (PNK), --.

Column 7, Line 23, delete "kinase (PNK)," and insert -- polynucleotide kinase (PNK), --.

Column 8, Line 8, delete "Oligo1" and insert -- Oligo 1 --.

Column 11, Line 14, delete "O-methylphosphoroamidite" and insert -- O-methylphosphoramidite --.

Column 11, Line 67, delete "(CIRCLIGASE;" and insert -- (CIRCLIGASE™; --.

Column 13, Line 9, delete "phophate" and insert -- phosphate --.

Column 13, Line 41-42, delete "(CIRCLIGASE')." and insert -- (CIRCLIGASE™). --.

Signed and Sealed this
Fourth Day of April, 2023

*Katherine Kelly Vidal*

Katherine Kelly Vidal
*Director of the United States Patent and Trademark Office*

Column 19, Line 65, delete "(CIRCLIGASE)." and insert -- (CIRCLIGASE™). --.

Column 21, Line 26 (approx.), delete "kinase (PNK)," and insert -- polynucleotide kinase (PNK), --.

Column 22, Line 40, delete "oligol-oligo2" and insert -- oligo 1-oligo 2 --.

Column 22, Line 41, delete "μmol" and insert -- pmol --.

Column 22, Line 43, delete "CIRCLIGASE" and insert -- CIRCLIGASE™ --.

Column 22, Line 50, delete "μmol" and insert -- pmol --.

Column 22, Line 61, delete "μmol" and insert -- pmol --.

SEQUENCE LISTING

```
<160> NUMBER OF SEQ ID NOS: 4

<210> SEQ ID NO 1
<211> LENGTH: 20
<212> TYPE: DNA
<213> ORGANISM: Artifical Sequence
<220> FEATURE:
<221> NAME/KEY: primer_bind
<222> LOCATION: (0)...(0)
<223> OTHER INFORMATION: P5 primer

<400> SEQUENCE: 1
aatgatacgg cgaccaccga                                              20

<210> SEQ ID NO 2
<211> LENGTH: 20
<212> TYPE: DNA
<213> ORGANISM: Artificial Sequence
<220> FEATURE:
<221> NAME/KEY: primer_bind
<222> LOCATION: (0)...(0)
<223> OTHER INFORMATION: P5' primer

<400> SEQUENCE: 2
tcggtggtcg ccgtatcatt                                              20

<210> SEQ ID NO 3
<211> LENGTH: 21
<212> TYPE: DNA
<213> ORGANISM: Artifical Sequence
<220> FEATURE:
<221> NAME/KEY: primer_bind
<222> LOCATION: (0)...(0)
<223> OTHER INFORMATION: P7 primer

<400> SEQUENCE: 3
caagcagaag acggcatacg a                                            21
```

```
<210> SEQ ID NO 4
<211> LENGTH: 21
<212> TYPE: DNA
<213> ORGANISM: Artificial Sequence
<220> FEATURE:
<221> NAME/KEY: primer_bind
<222> LOCATION: (0)...(0)
<223> OTHER INFORMATION: P7' primer

<400> SEQUENCE: 4
tcgtatgccg tcttctgctt g                                             21
```